United States Patent
Ishihara et al.

(10) Patent No.: US 8,921,114 B2
(45) Date of Patent: Dec. 30, 2014

(54) DIAGNOSIS SUPPORT SYSTEM FOR CANCER, DIAGNOSIS SUPPORT INFORMATION PROVIDING METHOD FOR CANCER, AND COMPUTER PROGRAM PRODUCT

(75) Inventors: Hideki Ishihara, Miki (JP); Tomoko Matsushima, Kobe (JP); Masaki Shibayama, Kobe (JP)

(73) Assignee: Sysmex Corporation, Hyogo (JP)

( * ) Notice: Subject to any disclaimer, the term of this patent is extended or adjusted under 35 U.S.C. 154(b) by 655 days.

(21) Appl. No.: 12/197,714

(22) Filed: Aug. 25, 2008

(65) Prior Publication Data
US 2009/0054739 A1 Feb. 26, 2009

(30) Foreign Application Priority Data

Aug. 24, 2007 (JP) ................................. 2007-219098
Jun. 30, 2008 (JP) ................................. 2008-171207

(51) Int. Cl.
 G06F 19/24 (2011.01)
 G06F 19/20 (2011.01)
 G06F 19/00 (2011.01)

(52) U.S. Cl.
 CPC ............... *G06F 19/24* (2013.01); *G06F 19/20* (2013.01)
 USPC ...................... 436/64; 600/300; 703/5; 703/3

(58) Field of Classification Search
 CPC ......... G06F 19/24; G06F 19/20; G06F 19/10; G06F 19/00
 USPC .............................. 436/64; 600/300; 703/5, 3
 See application file for complete search history.

(56) References Cited

U.S. PATENT DOCUMENTS

2002/0164678 A1 11/2002 Ganser et al.
2003/0233197 A1 12/2003 Padilla et al.

FOREIGN PATENT DOCUMENTS

| | | |
|---|---|---|
| EP | 1 767 647 A1 | 3/2007 |
| JP | 57-074663 A | 5/1982 |
| JP | 2005-058113 A | 3/2005 |
| JP | 2005-341862 A | 12/2005 |
| JP | 2006-223303 A | 8/2006 |
| JP | 2006-302113 | 11/2006 |
| WO | 99/42821 A2 | 8/1999 |
| WO | 00/01845 A2 | 1/2000 |
| WO | 03/078662 A1 | 9/2003 |
| WO | 2005/007846 A1 | 1/2005 |
| WO | 2005/116241 A1 | 12/2005 |

OTHER PUBLICATIONS

Pomeroy, S.L. et al., "Prediction of central nervous system embryonal tumour outcome based on gene expression," Nature, Jan. 24, 2002, pp. 436-442, vol. 415, No. 6870, Nature Publishing Group, London, UK, XP002356657.

Sinha, A.K., "Power system security assessment using pattern recognition and fuzzy estimation," International Journal of Electrical Power & Energy Systems, Feb. 1995, vol. 17, No. 1, pp. 11-19, XP-0025002466.

*Primary Examiner* — Christine T Mui
(74) *Attorney, Agent, or Firm* — Sughrue Mion, PLLC

(57) ABSTRACT

A diagnosis support system for cancer is disclosed that comprises: a measurement value acquiring section for acquiring a measurement value of a first cancer patient; a sample data memory for storing sample data of a plurality of cancer patients different from the first patient; a reference range determination section for determining a reference range based on the measurement value of the first cancer patient; a display unit; and a display controller for controlling the display unit to display a diagnosis support screen showing the clinical information included in the sample data having measurement value within the reference range. A method of providing cancer diagnosis support information and a computer program product are also disclosed.

25 Claims, 31 Drawing Sheets

DIAGNOSIS SUPPORT SYSTEM FOR CANCER, DIAGNOSIS SUPPORT INFORMATION PROVIDING METHOD FOR CANCER, AND COMPUTER PROGRAM PRODUCT

CROSS-REFERENCE TO RELATED APPLICATION

This application claims priority from Japanese Patent Application 2007-219098 filed on Aug. 24, 2007, and Japanese Patent Application 2008-171207 filed on Jun. 30, 2008. Each of the disclosure of these patent applications is herein incorporated by reference in its entirety.

TECHNICAL FIELD

The present invention relates to a diagnosis support system for cancer, diagnosis support information providing method for cancer, and a computer program product.

BACKGROUND

Serum diagnosis for examining the tumor marker in the serum, as well as tissue diagnosis and cell diagnosis by biopsy are conventionally known for cancer diagnosis. However, the reliability thereof is low, or the determination by individuals or determination by medical facilities varies. Thus, a molecular diagnosis based on genes and protein expressed in the living body is recently being reviewed as a standardized diagnosis method for cancer in which variation among diagnostician is small. Various methods such as a method of using cyclin-dependent kinase (hereinafter also simply referred to as "CDK") have been proposed as a molecular diagnosis based on protein (see e.g., International Publication WO 2005/116241 and International Publication WO 2003/078662).

International Publication WO 2005/116241 discloses a method of measuring a ratio obtained from an activity value and an expression level of the CDK1 (CDK1 specific activity) and a ratio obtained from an activity value and an expression level of the CDK2 (CDK2 specific activity), comparing CDK2 specific activity/CDK1 specific activity with a threshold value set in advance, and determining the malignancy of cancer based on such result. International Publication WO 2003/078662 discloses a method of normalizing the expression level of a predetermined gene such as p52BP2 gene, cathepsin B gene, cathepsin L gene, Ki67/MiB1 gene, thymidine kinase gene, and p27 gene, and an expression product thereof with respect to a control gene, and predicting the clinical result of the patient to compare with the amount derived in a reference cancer tissue set.

In the above methods, the predetermined threshold value set in advance and the measurement value of the parameter are compared, and the state of cancer is predicted and the clinical result is predicted based on the comparison result. However, in such methods, determination is made with the threshold value as the reference even if the measurement value of the parameter is very close to the threshold value. Thus, for example, even with a clinical sample that actually has a high recurrence risk, the determination result different from the actual result is sometimes obtained since the measurement value of the parameter obtained from the clinical sample is slightly lower than or greater than the threshold value. In this case, an accurate determination is not said to be made with the above method, and an accurate diagnosis may not be made if such determination result is used in diagnosis of cancer.

SUMMARY OF THE INVENTION

The scope of the present invention is defined solely by the appended claims, and is not affected to any degree by the statements within this summary.

A diagnosis support system for cancer embodying features of the present invention includes: a measurement value acquiring section for acquiring a measurement value of a first cancer patient, wherein the measurement value is generated by conducting measurement of a predetermined measurement item on a sample prepared by using a malignant tumor obtained from the first cancer patient; a sample data memory for storing sample data of a plurality of cancer patients different from the first patient, wherein the sample data comprise measurement values generated by conducting measurement of the predetermined measurement item on each sample prepared by using a malignant tumor obtained from each of the plurality of cancer patients, and clinical information after resection of malignant tumor of each of the plurality of the cancer patients; a reference range determination section for determining a reference range based on the measurement value of the first cancer patient acquired by the measurement value acquiring section, wherein the measurement value of the first cancer patient is within the reference range; a display unit; and a display controller for controlling the display unit to display a diagnosis support screen showing the clinical information included in the sample data having measurement value within the reference range.

A method of providing cancer diagnosis support information, using a system storing sample data of a plurality of cancer patients different from a first patient, wherein the sample data comprise measurement values generated by conducting measurement of a predetermined measurement item on each sample prepared by using a malignant tumor obtained from each of the plurality of cancer patients, and clinical information after resection of malignant tumor of each of the plurality of the cancer patients, embodying features of the present invention includes the steps of: acquiring a measurement value of the first cancer patient, wherein the measurement value is generated by conducting measurement of the predetermined measurement item on a sample prepared by using a malignant tumor obtained from the first cancer patient; determining a reference range based on the measurement value of the first cancer patient, wherein the measurement value of the first cancer patient is within the reference range; and displaying a diagnosis support screen showing clinical information included in the sample data having measurement value within the reference range.

A computer program product embodying features of the present invention includes: a computer readable medium; and instructions, on the computer readable medium, adapted to enable a computer to perform operations, comprising: acquiring a measurement value of a first cancer patient, wherein the measurement value is a measurement value generated by conducting measurement of a predetermined measurement item on a sample prepared by using a malignant tumor obtained from the first cancer patient; storing sample data of a plurality of cancer patients different from the first patient, wherein the sample data comprise measurement values generated by conducting measurement of the predetermined measurement item on each sample prepared by using a malignant tumor obtained from each of the plurality of cancer patients, and clinical information after resection of malignant tumor of each of the plurality of the cancer patients; determining a reference range based on the measurement value of the first cancer patient, wherein the measurement value of the first cancer patient is within the reference range; and displaying a diagnosis support screen showing the clinical information included in the sample data having measurement value within the reference range.

DETAILED DESCRIPTION OF THE PREFERRED EMBODIMENTS

Figure 1:
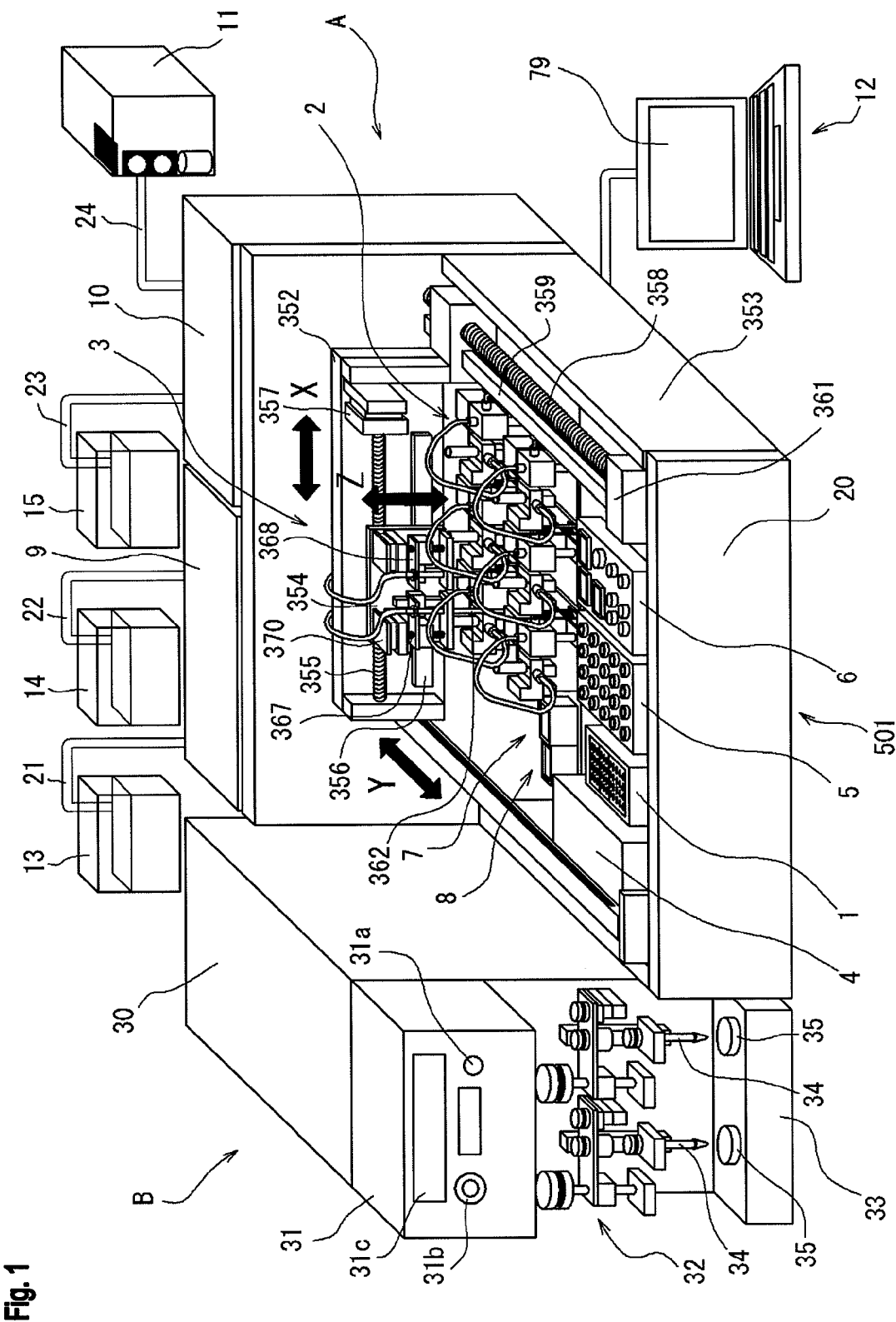
FIG. 1 is a perspective explanatory view of one embodiment of a diagnosis support system of the present invention.

An embodiment of a diagnosis support system for cancer (hereinafter also referred to simply as "diagnosis support system") of the present invention will now be described in detail with reference to the accompanying drawings. The diagnosis support system of the present embodiment provides information for supporting the diagnosis of cancer based on sample data in which the measurement value of a predetermined measurement item related to a malignant tumor of a cancer patient to be diagnosed and the measurement value of the predetermined measurement item related to the malignant tumor of other cancer patients, and clinical information after resection of malignant tumor of the other cancer patients.

Malignant tumors are tumors that invade or metastasize to other tissues, and enlarge at various sites of the body thereby threatening the human life. The malignant tumor includes cancer or malignant tumor originating from epithelial tissue, and sarcoma or malignant tumor originating from non-epithelial tissue. Specifically, the malignant tumor includes malignant tumors forming at positions such as breast, lung, liver, stomach, large intestine, pancreas, uterus, testis, ovaria, thyroid, accessory thyroid, lymphography, and the like. The malignant tumor can be obtained from cancer patients having breast cancer, lung cancer, liver cancer, gastric cancer, large intestine cancer, pancreas cancer, prostate cancer, and the like.

In the diagnosis support system of the present embodiment, the clinical information on other cancer patients having a measurement value approximate to the measurement value of the predetermined measurement item related to the malignant tumor of the cancer patient to be diagnosed can be provided as information (hereinafter also referred to as "cancer diagnosis support information") for supporting the diagnosis on the cancer patient to be diagnosed. The clinical information provided by the diagnosis support system contains information on the presence/absence of recurrence of the other cancer patients having the measurement value within a reference range. In the diagnosis support system, information such as the recurrence rate or the disease free survival calculated based on the information on the presence/absence of recurrence of the other cancer patients having the measurement value within the reference range can be provided as the clinical information.

Furthermore, in the diagnosis support system of the present embodiment, the malignancy of cancer is determined based on the measurement value of the predetermined measurement item related to the malignant tumor of the cancer patient to be diagnosed, and such determination result can be also provided as the cancer diagnosis support information along with the clinical information on the other cancer patients. The malignancy of cancer specifically includes likelihood to metastasize, likelihood to recur, unsatisfactory prognosis, and the like.

The predetermined measurement item measured in the diagnosis support system of the present embodiment is not particularly limited as long as it is a measurement item related to gene and/or protein in the malignant tumor, and the type of gene or protein and the type of measurement item are appropriately selected depending on the type of cancer, the diagnosis support information to provide, or the like.

The predetermined measurement item includes measurement value related to CDK disclosed in International Publication WO 1999/042821, International Publication WO 2000/001845, US Patent Application Publication 2002-164673, International Publication WO 2005/116241, and the like. Specifically, the measurement value related to the CDK includes expression level of CDK, activity value of CDK, ratio of the activity value and the expression level of the CDK (e.g., specific activity, inverse number of the specific activity), and the like. In addition to the CDK, the predetermined item may be the expression level of the gene used to predict the recurrence risk of the cancer in Japanese Laid-Open Patent Publication No. 2005-58113, Japanese Laid-Open Patent Publication No. 2006-223303, International Publication WO 2003/078662, and the like. The predetermined measurement item may be the expression level of the gene used to predict the receptivity of anticancer drug in International Publication WO 2005/007846, Japanese Laid-Open Patent Publication No. 2005-341862, and the like.

The diagnosis support system of the present embodiment will now be described with reference to, as an example, a diagnosis support system for measuring the expression level and the activity value of the CDK in the malignant tumor obtained from the cancer patient, and providing information related to malignance of cancer (likelihood to recur) based on the obtained measurement value.

Prior to describing the diagnosis support system, [1] usability of CDK in diagnosing cancer will be described.

[1] Usability of CDK in Diagnosing Cancer

The measurement value related to cyclin-dependent kinase (CDK) accurately reflects the state of malignant tumor in a patient with cancer. Thus, the expression level and the activity value of two or more types of cyclin-dependent kinase in a tissue containing malignant tumor can be measured, and nature of the tissue containing the relevant malignant tumor, the likelihood of the cancer to recur, and the like can be evaluated based on the ratio of the activity value and the expression level of a first CDK and the ratio of the activity value and the expression level of a second CDK. The measurement value related to the CDK indicates the similar measurement value in cancer patients having malignant tumor of similar states. Thus, for example, the expression level and the activity value of two or more types of cyclin-dependent kinase in a tissue containing malignant tumor can be measured, and nature of the tissue containing the relevant malignant tumor, the likelihood of the cancer to recur, and the like can be diagnosed based on the ratio of the activity value and the expression level of a first cyclin-dependent kinase and the ratio of the activity value and the expression level of a second cyclin-dependent kinase.

Therefore, as the measurement value related to the CDK, the ratio of the activity value and the expression level of at least one type of CDK of a certain tissue (e.g., specific activity), and/or a numerical value calculated with the activity value and the expression level of a plurality of CDKs (e.g., ratio (e.g., "A1/A2" or "A2/A1") of the ratio (A1) of the activity value and the expression level of the first CDK and the ratio (A2) of the activity value and the expression level of the second CDK) can be used.

Here, recurrence refers to a case where the same malignant tumor reappears in the remaining organs after an organ is partially removed to resect the malignant tumor, and a case where the tumor cell is separated from a primary tumor and conveyed to a remote tissue (remote organ), and independently grows thereat (metastasize and recur). Generally, "likely to recur" refers to a case where there is a possibility the cancer will recur within five years after the resection surgery. Since the death rate of the patients recognized with recurrence within five years is high, predicting the recurrence within five years after the resection surgery has clinical meaning. In stage classification, stage III has a recurrence rate of 50%, and recurrence is likely to occur compared to stage II (recurrence rate of 20%).

The cyclin-dependent kinase is a collective term of a phosphoenzyme group activated by being bounded to cyclin, and functions in a specific time of the cell cycle depending on the type thereof. The CDK inhibitor is a collective term of a factor group that bonds with the cyclin CDK complex and inhibits the activity of the cyclin CDK complex.

Figure 14:
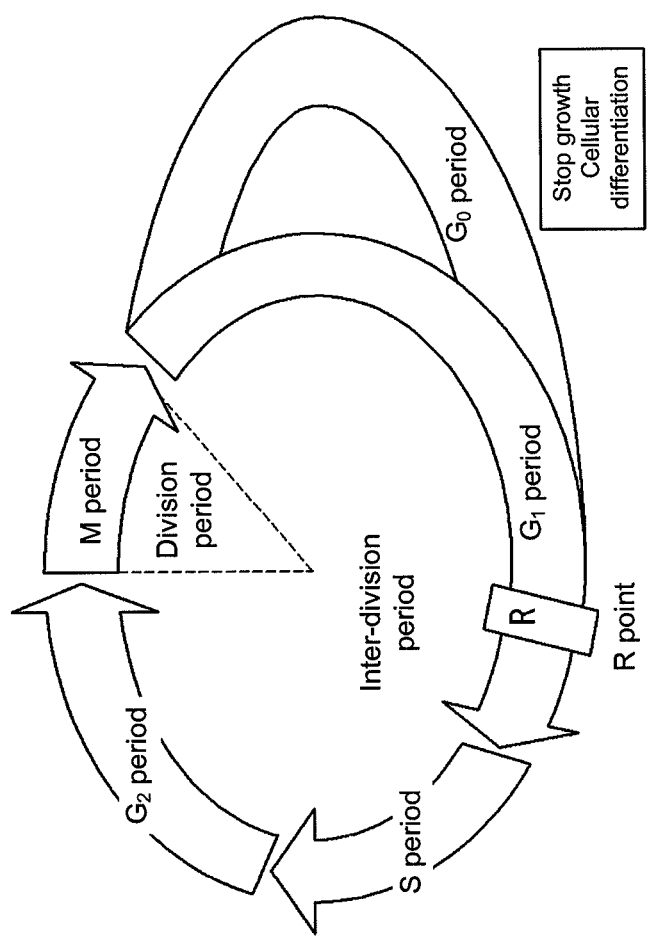
FIG. 14 is a schematic view describing a cell cycle.
Figure 15:
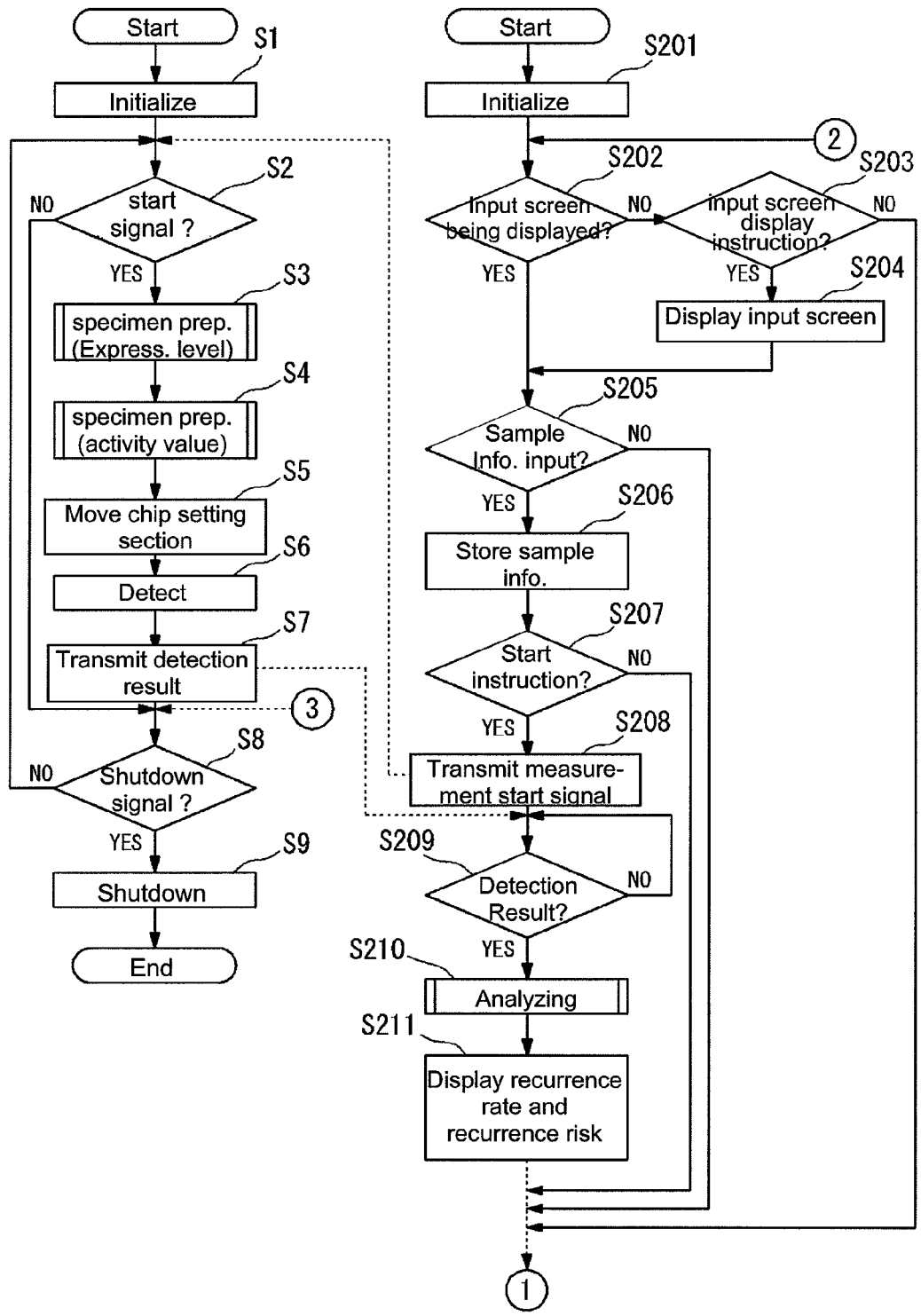
FIG. 15 is a view showing an overall flow of one example of a process by the diagnosis support system.
Figure 16:
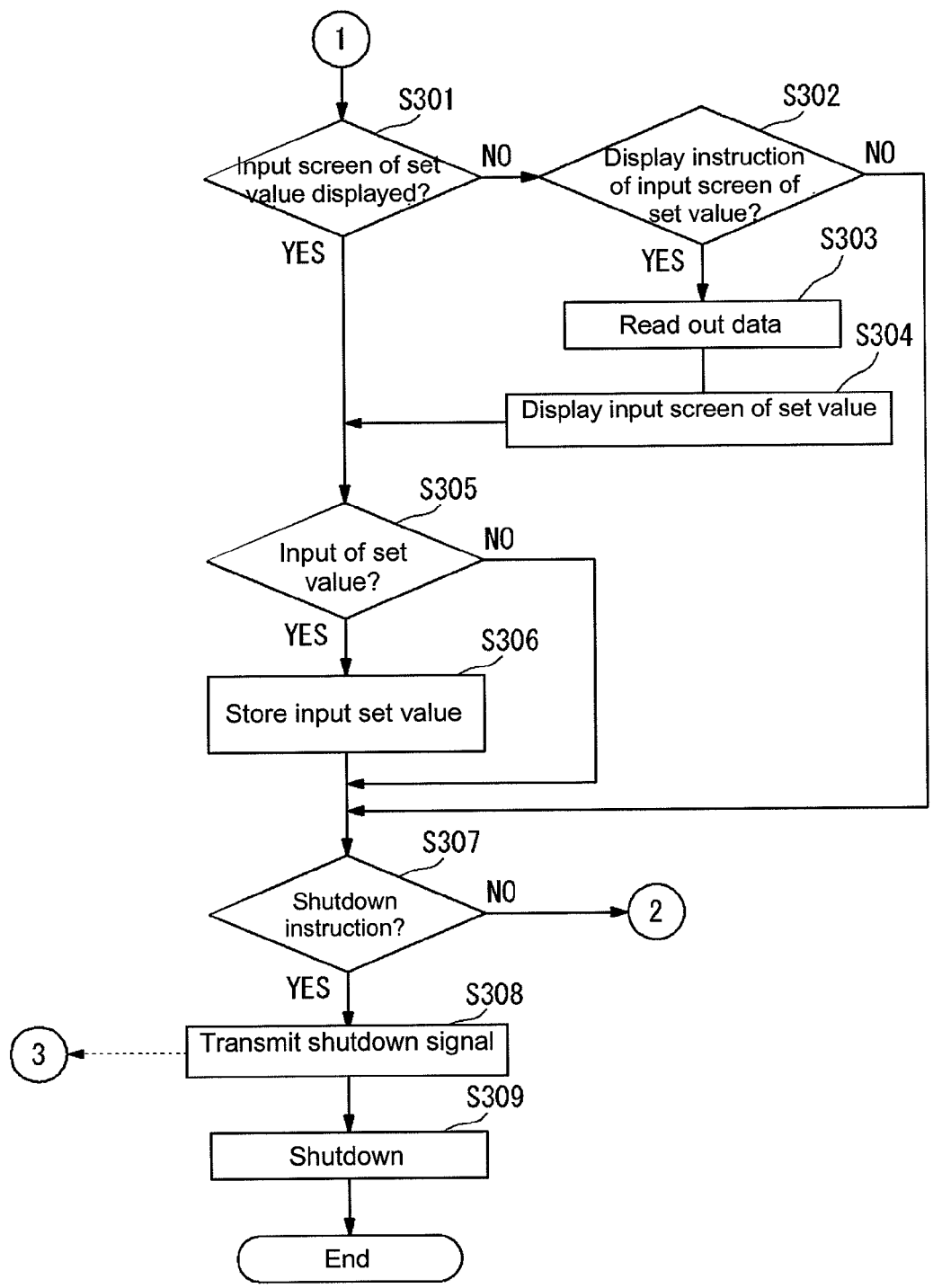
FIG. 16 is a view showing an overall flow of one example of a process by the diagnosis support system.

The cell cycle is a cycle in which the cell starts to grow and return to the starting point as two daughter cells after events of DNA replication, distribution of chromosomes, nuclear division, cytoplasmic division, and the like. The cell cycle is divided into four periods of $G_1$ period, S period, $G_2$ period, and M period, as shown in FIG. 14. The S period is the replication period of the DNA, and the M period is the division period. The $G_1$ period is a preparation period for the cell to enter the S period from the completion of mitotic division to the start of DNA synthesis. After passing a critical point (point R in animal cell) in the $G_1$ period, the cell cycle starts, and normally completes one cycle without stopping in the middle. The $G_2$ period is a period from the termination of the DNA synthesis to the start of mitotic division, and is a preparation period for the cell to enter the M period. Main check points of the cell cycle are immediately before entering the S period from the $G_1$ period ($G_1$ check point), and the transition period ($G_2$/M check point) from the $G_2$ period to mitotic division. In particular, the $G_1$ check point is important as it is related to the start of the S period. This is because, after passing a certain point of the $G_1$ period, the cell advances the cell cycle as S period→$G_2$ period→M period→$G_1$ period without stopping the growth even if a growth signal is not provided. The cell that has stopped growing enters a rest period ($G_0$ period) having DNA content of the $G_1$ period, and is on the state deviating from the cell cycle. Due to growth induction in the $G_0$ period, the cell can advance to the S period after a time slightly longer than the $G_1$ period in the cell cycle.

The cyclin-dependent kinase (CDK) used in the determining method is not particularly limited, but may be CDK1, CDK2, CDK4, CDK6, and the like. The CDK also includes CDK belonging to cyclin A-dependent kinase, CDK belonging to cyclin B-dependent kinase, CDK belonging to cyclin D-dependent kinase, CDK belonging to cyclin E-dependent kinase, and the like. The cyclin A-dependent kinase may be a CDK that indicates activity by being bound to cyclin A, and is not particularly limited but includes CDK1, CDK2, and the like. The cyclin B-dependent kinase may be a CDK that indicates activity by being bound to cyclin B, and is not particularly limited but includes CDK1 and the like. The cyclin D-dependent kinase may be a CDK that indicates activity by being bound to cyclin D, and is not particularly limited but includes CDK4, CDK6, and the like. The cyclin E-dependent kinase may be a CDK that indicates activity by being bound to cyclin E, and is not particularly limited but includes CDK2 and the like.

Such CDK activates a predetermined period of the cell cycle as shown in table 1 by being a cyclin-CDK complex (hereinafter also referred to as "active CDK") bound to the corresponding cyclin, as shown in table 1. For instance, CDK1 becomes active by binding to cyclin A or B, CDK2 becomes active by binding to cyclin A or E, and CDK4 and CDK6 become active by binding to cyclin D1, D2, or D3. The CDK activity sometimes has the activity inhibited by the CDK inhibitor as shown in table 1. For instance, p21 inhibits CDK1 and CDK2, p27 inhibits CDK2, CDK4, and CDK6, and p16 inhibits CDK4 and CDK6.

TABLE 1

| | Binding cyclin | Binding CDK inhibitor | Operating period of active CDK |
|---|---|---|---|
| CDK4 | Cyclin D1 | p27, p16 | $G_1$ period |
| CDK6 | Cyclin D2 Cyclin D3 | | |
| CDK2 | Cyclin E | p27 | $G_1 \to$ S transition |
| CDK2 | Cyclin A | p21, p27 | S period active |
| CDK1 | Cyclin A Cyclin B | p21 | $G_1 \to$ M transition |
| Cyclin A-dependent kinase | Cyclin A | p21, p27 | CDK1: $G_2$ period $\to$ M period CDK2: middle period of S period |
| Cyclin B-dependent kinase | Cyclin B | p21 | CDK1: $G_2$ period $\to$ M period |
| Cyclin D-dependent kinase | Cyclin D | p27, p16 | CDK4, CDK6: $G_1$ period |

Of the CDKs, the expression level and the activity level of two or more types of CDK are measured, the ratio (CDK specific activity or inverse number thereof expressed by the following equation) of the expression level and the activity value in each CDK is obtained.

Specific activity of CDK=CDK activity value/CDK expression level

The CDK activity value refers to the level (unit is expressed as U (unit)) of the kinase activity indicated by the amount of substrate that binds with a predetermined cyclin, and phosphorylates. The substrate to which the CDK phosphorylates includes histon H1 for active CDK1 and active CDK2, and Rb (retinoblastoma protein) for active CDK4 and active CDK6. The CDK activity value can be measured with a conventionally known enzyme activity measurement method. Specifically, there may be a method of preparing a specimen containing the active CDK from the cell dissolved solution of the measurement specimen, retrieving $^{32}P$ into the substrate protein by using the relevant specimen and the $^{32}P$ labeled ATP ($\gamma$-[$^{32}$]-ATP), measuring the labeled quantity of the $^{32}P$ labeled phosphorylated substrate, and determining the quantity based on the standard curve created with a standard product. A method that does not use label of the radioactive substance includes the method disclosed in Japanese Laid-Open Patent Publication No. 2002-335997. This method is a method of preparing a specimen containing the target active CDK from the cell solubilizing solution of the measurement specimen, reacting adenosine 5'-O-(3-thiotriphosphate) (ATP-$\gamma$S) and the substrate protein, introducing monothiophosphate group to serine residue or threonine residue of the substrate protein, bonding labeled fluorescence substance or labeled enzyme to the sulfur atom of the introduced monothiophosphate group to label the substrate protein, measuring the labeled quantity (fluorescence quantity when labeled fluorescence substance is used) based on the labeled thiophosphate group, and determining the quantity based on the standard curve created with the standard product.

The specimen provided for activity measurement is prepared by specifically collecting the target CDK from the solubilizing solution of the tissue containing the malignant tumor to be measured. In this case, the specimen may be prepared using an anti-CDK antibody specific for the target CDK, or prepared using an anti-cyclin antibody in a case of activity measurement of a predetermined cyclin-dependent kinase (e.g., cyclin A-dependent kinase, cyclin B-dependent kinase, and cyclin E-dependent kinase). In either case, CDK other than the active CDK will be contained in the specimen. For instance, a complex in which the CKD inhibitor is bound to the cyclin CDK complex is also included. When the anti-CDK antibody is used, CDK single body, complex of CDK as well as cyclin and/or CDK inhibitor, complex of CDK and another compound, and the like are contained. Therefore, the activity value is measured as a unit (U) of phosphorylated substrate under a state that active type, non-active type, and various competitive reaction coexist.

The CDK expression level is the target CDK level (unit corresponding to number of molecules) measured from the cell solubilizing solution, and is measured with a conventionally known method of measuring the target protein quantity from the protein mixture. For instance, ELISA method, western blot method, and the like may be used, or measurement may be carried out with a method disclosed in Japanese Laid-Open Patent Publication No. 2003-130871. The target protein (CDK) is captured using a unique antibody. For instance, all of the CDK1 existing within the cell (include CDK single body, complex of CDK as well as cyclin and/or CDK inhibitor, complex of CDK and another compound) can be captured using the anti-CDK1 antibody.

Therefore, the specific activity calculated from the above equation corresponds to the proportion of the CDK indicating activity of the CDK existing within the cell, and is the CDK activity level based on the growth state of the malignant tumor cell to be determined. The CDK specific activity obtained in this manner does not depend on the measurement specimen preparation method. In particular, the measurement specimen (cell solubilizing solution) prepared from the biopsy material is likely to be influenced by the size of non-cellular tissues such as extracellular matrix contained in the actually collected tissue. Therefore, there is a large meaning of using the specific activity or the inverse number thereof in which such influence is eliminated, and the correlation with the clinical characteristics is high as compared to the conventional simple activity value.

If the CDK specific activity or the inverse number thereof of two or more types is known, which CDK activity is superior can be known, whereby the extent of the cell proportion in the periods of the cell cycle can be known, or the cell proportion of which period is superior can be known.

The type of CDK for measuring the specific activity is not particularly limited, and may be appropriately selected. Generally, since the cancer cells actively grow deviating from the normal growth control, cell proportion in the S period and the $G_2$ period is considered to be large. It is therefore considered that the cells become cancerous in such case. The progression of such cancer is fast, and thus such cancer is malignant. Furthermore, aneuploid medium is considered to occur when an abnormal M period has elapsed or the cell enters the $G_1$ period without going through the M period and then entering the S period. Thus, the cancer is assumed to be malignant when the cell proportion in the M period is small. Therefore, the CDK1 is used as the first cyclin-dependent kinase and the CDK2 is used as the second cyclin-dependent kinase, classification to groups is carried out according to the magnitude of the CDK1 specific activity, and the CDK2 specific activity value takes a value reflecting the cell ratio of the S period of the groups having a similar CDK1 specific activity. When cells are in great numbers in the S period, the tissue where the cells are configuring cells can be determined as clinically malignant, that is, as a malignant cancer that is likely to metastasize and has poor prognosis.

Therefore, in the diagnosis support system of the present embodiment, information useful for diagnosis of the cancer patient to be diagnosed is provided by obtaining the specific activity of two or more types of CDK for the cancer patient to be diagnosed, and providing clinical information on other cancer patients having a CDK specific activity approximate to the CDK specific activity of the cancer patient.

[2] Diagnosis Support System

The diagnosis support system according to one embodiment of the present invention will be described below. The diagnosis support system according to the present embodiment uses the CDK1 specific activity and the CDK2 specific activity described above as measurement values of a predetermined measurement item. Specifically, the diagnosis support system according to the present embodiment acquires the expression levels and the activity values of the CDK1 and the CDK2 of the subject cancer patient. The CDK1 specific activity and the CDK2 specific activity are calculated from the acquired expression levels and the activity values of the CDK1 and CDK2. A reference range is determined based on the calculated CDK1 specific activity and the CDK2 specific activity. The sample data of other cancer patients having the CDK1 specific activity and the CDK2 specific activity within the reference range is searched from the sample data of other cancer patients stored in advance, and specified. The recurrence rate is calculated based on the specified sample data, and the risk of recurrence is determined based on the calculated recurrence rate. A screen including the result of the calculated recurrent rate and the determination result of the recurrence risk is generated, and the generated screen is displayed on the display unit.

FIG. 1 is a perspective explanatory view of a diagnosis support system according to one embodiment of the present invention. The diagnosis support system according to the present embodiment is configured by a measuring device A and a solubilizing device B. The measuring device A is configured by a measurement unit 501 and a data processing unit 12. The measuring unit 501 measures the activity value and the expression level of the CDK1 as well as the activity value and the expression level of the CDK2, and is mainly configured by a detecting section 4 arranged at the front portion of an apparatus body 20; a tip setting section 1; first reagent setting section 5 and second reagent setting section 6; an activity measurement unit 2 arranged at a back portion of the apparatus body 20; a waste bath 7 for accommodating waste liquid and a pipette washing bath 8 for washing pipette; a dispensing mechanism section 3 arranged on the upper side of the apparatus body 20, for moving the pipette in three directions (X direction, Y direction, and Z direction); and a fluid section 9 and a body controller 10 arranged at the back part of the apparatus body 20. The data processing unit 12 is communicably connected to the body controller 10. A pure water tank 13, a washing liquid tank 14, a waste tank 15, and a pneumatic source 11 are arranged in the measuring device A. The pure water tank 13 stores pure water for washing a flow channel at the end of measurement and is connected to the fluid section 9 with a conduit 21; the washing liquid tank 14 stores washing liquid for washing the pipette and is connected to the pipette washing bath 8 with a conduit 22; and the waste tank 15 for accommodating the waste liquid is connected to the waste bath 7 with a conduit 23. The solubilizing device B for obtaining a sample that can be processed in the measuring device A from a biological specimen is arranged next to the measuring A.

The solubilizing device B and the measuring device A will be described below in order.

[Solubilizing Device]

The solubilizing device B prepares a liquid sample that can be processed in the measuring device A from the biological specimen such as the tissue resected from the patient, prior to the process by the measuring device A, and is mainly configured by a housing 30, an operating section 31 arranged on the upper side at the front surface of the housing 30, a driving section 32 including a pair of pestles 34 for pressing and grinding the biological specimen, and a sample setting section 33 to be set with a container 35 accommodating the biological specimen.

The driving section 32 moves the pestles 34 in the up and down direction, and provides rotational movement thereto, so that the biological specimen injected into the container 35 is pressed and grinded. A controller (not shown) for controlling the operation of the driving section 32 is built in the housing 30.

An operation button 31a, an operation lamp 31b, and a display part 31c for displaying the state of the apparatus and error message are arranged on the operating section 31. A cooling means (not shown) is arranged in the sample setting section 33 to maintain the biological specimen in the container set in a concave area of the upper surface of the sample setting section 33 at a constant temperature.

The supernatant solution of the biological specimen solubilized by the solubilizing device B and subjected to centrifugal process by a centrifugal machine (not shown) is collected to a predetermined sample container and set in a first reagent setting section 5 of the measuring device A.

[First Reagent Setting Section]

A cooling means (not shown) is arranged in the first reagent setting section 5, similar to the sample setting section 33, to maintain the sample, the CDK1 antigen (calibration 1), the CDK2 antigen (calibration 2), the fluorescent labeled CDK1 antibody, the fluorescent labeled CDK2 antibody and the like in the container set in the concave area of the upper surface of the first reagent setting section 5 to a constant temperature. In the present embodiment, a total of 20 concave areas are formed in a matrix of five by four, so that up to 20 containers can be set.

[Second Reagent Setting Section]

A second reagent setting section 6 is arranged next to the first reagent setting section 5. A plurality of concave areas is formed in the second reagent setting section 6, similar to the first reagent setting section 5. The containers with buffer, substrate solution, fluorescent enhancement reagent are set in the concave areas.

Prior to the process by the measuring device A, the solid phase tip for protein is set in the tip setting section 1, and the column is set in the activity measurement unit 2.

[Tip Setting Section]

Figure 2:
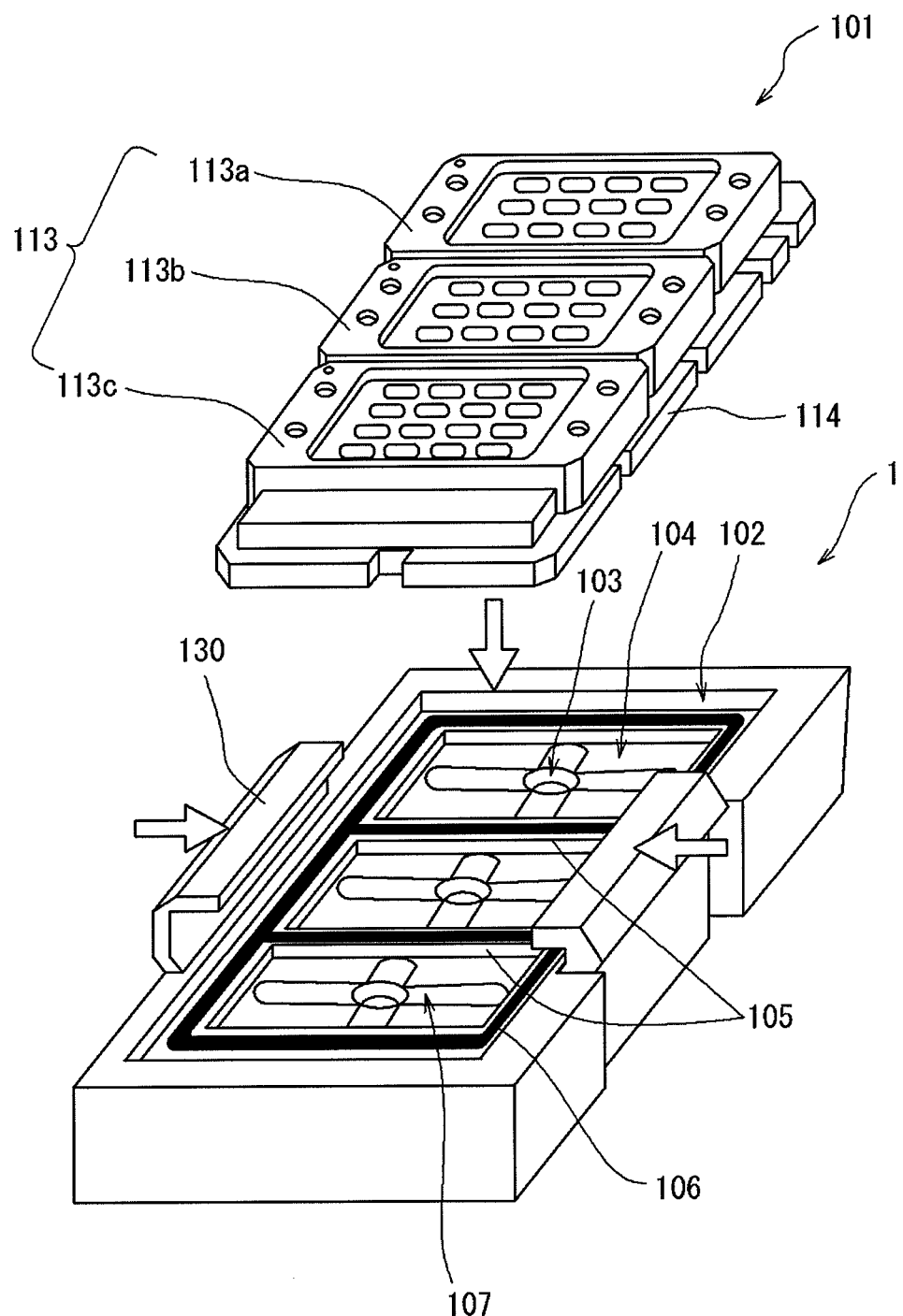
FIG. 2 is a perspective explanatory view of a tip setting section and a solid phase tip for protein in the diagnosis support system shown in FIG. 1.
Figure 3:
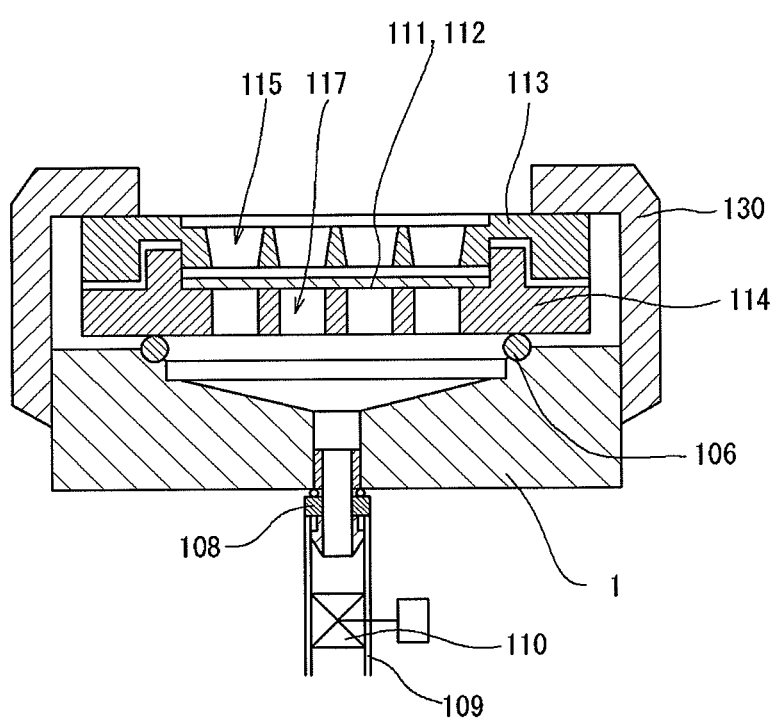
FIG. 3 is a cross sectional explanatory view of the tip setting section and the solid phase tip for protein in the diagnosis support system shown in FIG. 1.

The tip setting section 1 is made up of aluminum blocks, has a concave part 102 for mounting the solid phase tip for protein 101 at the upper surface, and has three aspiration ports 103 at the bottom part, as shown in FIGS. 2 and 3. More specifically, the tip setting section 1 includes a first concave part 102 of rectangular shape at the upper surface, and three second concave parts 104 also of rectangular shape at the bottom of the first concave part 102. The second concave parts 104 are independent from each other via a partition wall 105 so as to be in a non-communicating state when the solid phase tip for protein 101 is mounted on the tip setting section 1. A rubber elastic gasket 106 having rectangular frame shape is arranged at the peripheral edge of the second concave part 104 at the bottom surface of the first concave part 102.

The second concave part 104 includes a cross-shaped groove 107 at the bottom part and the aspiration port 103 at the center of the bottom part, wherein the bottom of the groove 107 is inclined so as to become deeper towards the center from the peripheral edge of the second concave part 104. The three aspiration ports 103 communicate with a nipple 108 arranged to connect to an external aspiration pneumatic source 11. A tube 109 having one end connected to the aspiration pneumatic source 11 side has the other end connected to the nipple 108. An open/close valve 110 is arranged in the tube 109.

The solid phase tip for protein 101 to be hereinafter described in detail is mounted horizontally at the bottom surface of the first concave part 102 by way of a gasket 106. The aspiration pump is activated after the protein containing specimen solution is injected or dropped into each well of the solid phase tip for protein 101.

The solid phase tip for protein 101 is then air tightly attracted to the bottom surface of the first concave part 102 by way of the gasket 106, and the specimen solution in each well is aspirated through the porous film to be hereinafter described, whereby the protein to be measured is solid phase formed on the porous film. In FIGS. 2 and 3, 130 is a pressing mechanism for pressing and fixing the solid phase tip for protein 101 to the bottom surface of the first concave part 102. The pressing mechanism 130 is sled in a direction of the arrow in the figure after the solid phase tip for protein 101 is mounted on the first concave part 102, so that the upper part thereof presses the upper surface of the solid phase tip for protein 101 and fixes the same to the first concave part 102.

Figure 4:
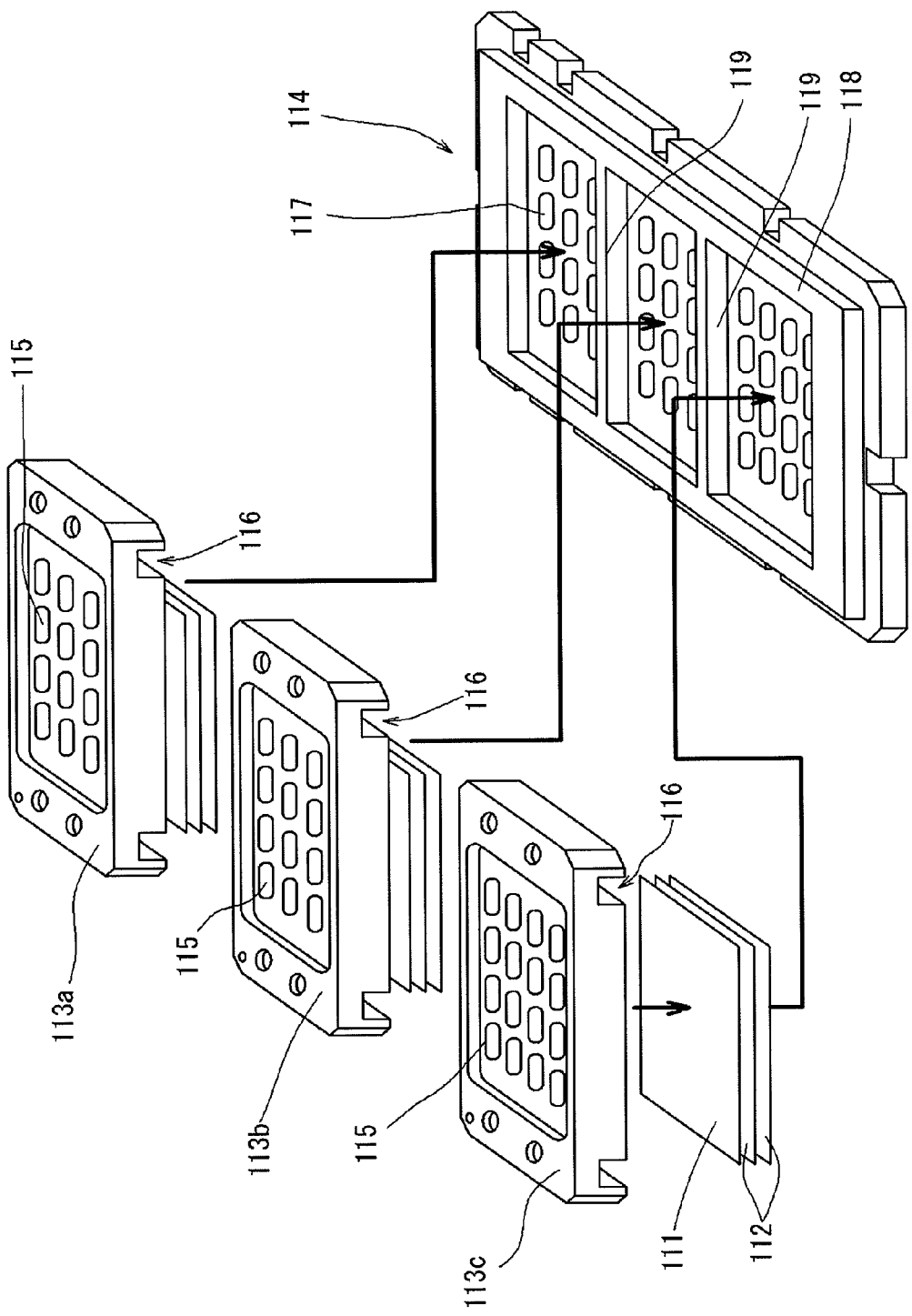
FIG. 4 is an exploded explanatory view of an upper plate and a lower plate of the solid phase tip for protein.
Figure 5:
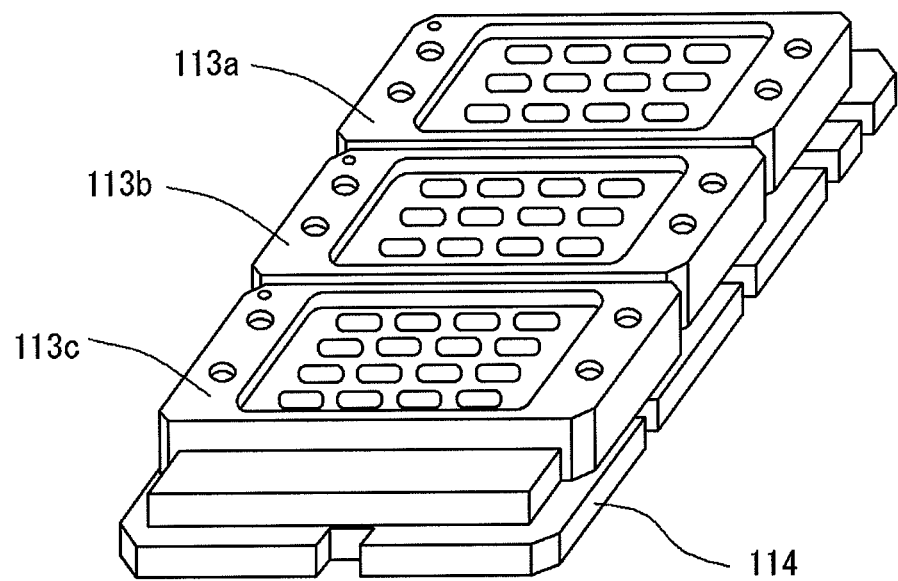
FIG. 5 is a perspective explanatory view of the solid phase tip for protein with the upper plate attached to the lower plate.

As shown in FIGS. 4 and 5, the solid phase tip for protein 101 is configured by a porous film 111 and a filter paper 112, and upper plate 113 and lower plate 114 for sandwiching and holding the porous film 111 and the filter paper 112. The solid phase tip for protein 101 has a function of contacting the antibody solution containing antibody of cyclin-dependent kinase and the biological specimen (sample).

As shown in FIGS. 4 and 5, the upper plate 113 is configured by three plates independent from each other, that is, a first upper plate 113a, a second upper plate 113b, and a third upper plate 113c. Each upper plate has a rectangular plate shape, wherein the first upper plate 113a and the second upper plate 113b are both formed with twelve oval through holes 115 arrayed in a matrix form of four by three, and the third upper plate 113c is formed with sixteen oval through holes 115 arrayed in a matrix form of four by four. Each upper plate includes a region, which is independent from each other for specimen processing, formed with a plurality of through holes. A groove 116 is formed along a short side at the bottom surface of each upper plate.

A total of forty oval through holes 117 arrayed in a matrix form is formed in the lower plate 114 having a rectangular plate shape at positions corresponding to each through hole 115 of the upper plates 113a, 113b, 113c. The through holes 117 have the same shape and cross sectional area as the through holes 115. The lower plate 114 has a region formed with a plurality of through holes corresponding to each region of the upper plates 113a, 113b, 113c.

A rib-shaped convex part 118 that goes around the periphery of the forty through holes 117 once, and a partition wall 119 for partitioning the through holes 117 to three regions in correspondence to each region of the upper plate 113a, 113b, 113c are formed on the upper surface of the lower plate 114. Three rectangular porous film installing regions are partitioned on the inner side by the convex part 118 and the partition wall 119. The upper plate 113 and the lower plate 114 are made of vinyl chloride resin and the like.

As shown in FIGS. 2 to 5, a stacked body including the porous film 111 and the filter paper (filter) 112 is mounted on the porous film installing region of the lower plate 114, and the grooves 116 of each upper plate 113a, 113b, 113c are sequentially fitted to the corresponding convex part 118 of the lower plate 114, so that the upper plates 113a, 113b, 113c are attached to the lower plate 114 thereby forming the solid phase tip for protein 101. Each through hole 115 and each through hole 117 then become coaxial to each other.

The solid phase tip for protein described above has the upper plate divided into three, so that three regions can be aspirated independently, but the number of upper plates may be two, or four or more, and is not particularly limited in the present invention. The number of upper plates is appropriately selected in view of the number of measurement items and the number of samples.

[Activity Measuring Specimen Preparation Unit]

As shown in FIGS. 6 to 10, the activity measuring specimen preparation unit 2 includes a plurality of specimen preparation sections 211 each including a column 201 and a fluid manifold 213, and is used to measure the activity value of the CDK.

Figure 6:
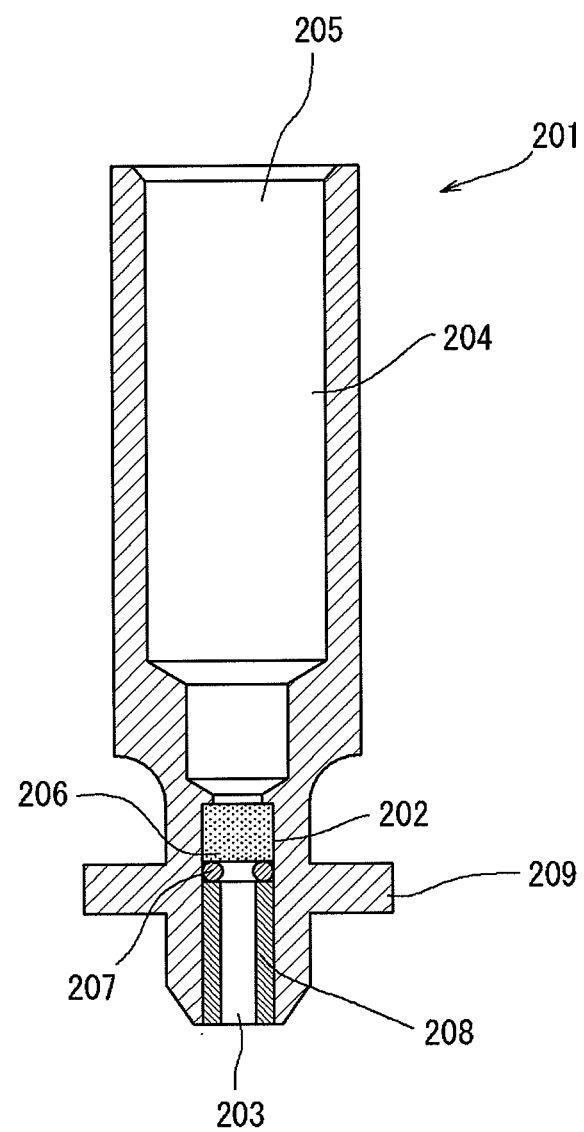
FIG. 6 is a cross sectional explanatory view of a column of a specimen preparation section of an activity measurement unit in the diagnosis support system shown in FIG. 1.

The column 201 shown in FIG. 6 is made of a cylindrical body made of vinyl chloride resin, and includes therein a carrier holding section 202 for holding a carrier 206 used to isolate the target substance in the liquid specimen, and a liquid storage section 204 for receiving and storing the liquid specimen to introduce the liquid specimen to the carrier holding section 202. The column 201 has an opening 205 through which the liquid sample is externally injected or the liquid specimen is injected or collected from the outside at the upper part of the liquid storage section 204, and includes a connection flow channel 203 for introducing the liquid specimen to the fluid manifold 213 and receiving the liquid specimen from the fluid manifold 213 at the lower part of the carrier holding section 202. The column 201 configures a means for contacting the substrate solution containing a predetermined substrate and the biological specimen (sample).

The carrier 206 is made of monolithic silica gel having circular cylinder shape, wherein the monolithic silica gel has a configuration in which the three-dimensional network frame work and the clearance thereof are integrated, as opposed to the particle carrier. The predetermined CDK antibody is immobilized to the monolithic silica gel. The carrier 206 is inserted to the carrier holding section 202 from the lower opening of the column 201, and is elastically pushed and supported by a fixing pipe 208 by way of an O-ring 207. The fixing pipe 208 is press-fit from the lower opening of the column 201, wherein the holes of the fixing pipe 208 and the O-ring 207 form the connection flow channel 203.

A mounting flange 209 for mounting and fixing the column 201 to the specimen preparation section 211 is formed at the lower end of the column 201. The flange 209 is an oval flange formed by cutting out both sides of a disc shaped flange having a diameter D in parallel so as to have a width W (W<D).

Figure 7:
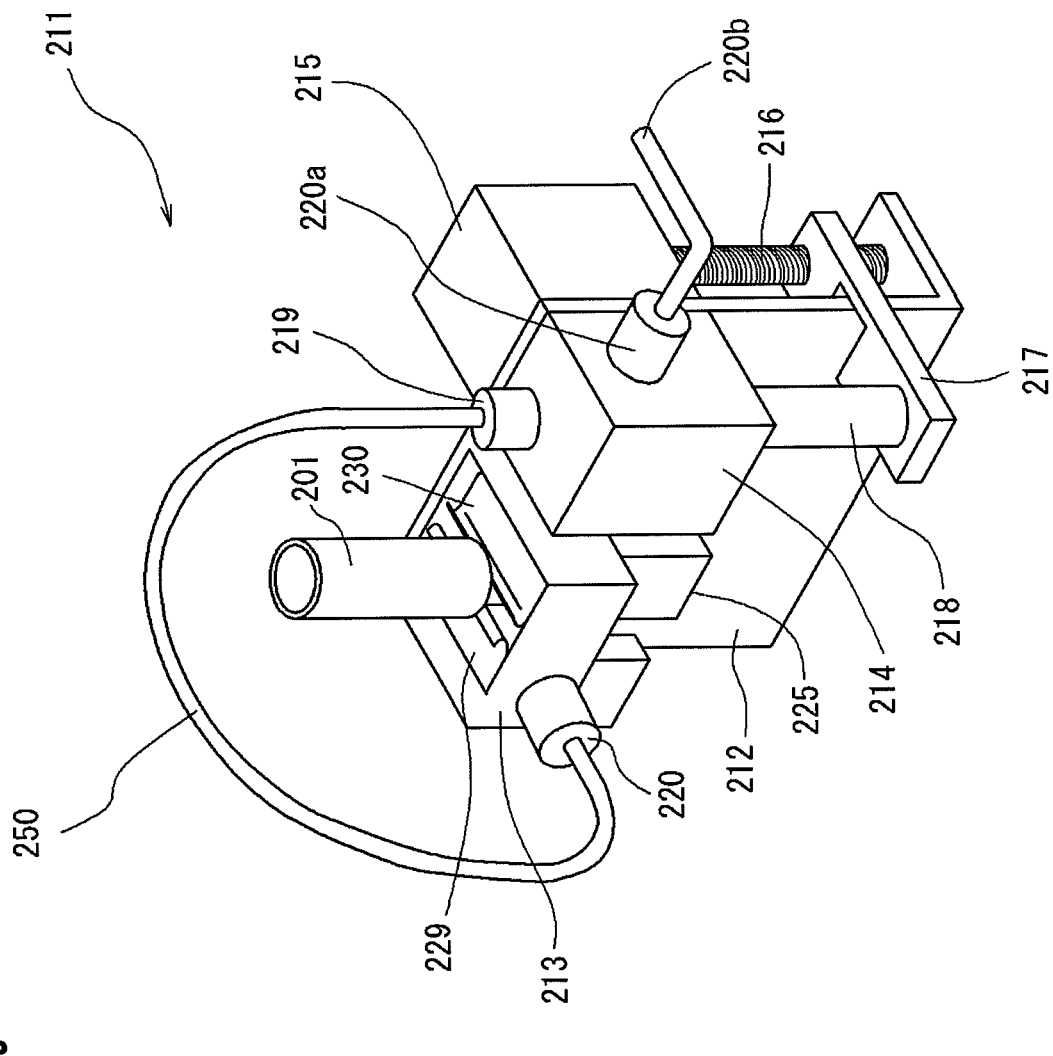
FIG. 7 is a perspective view of the specimen preparation section of the activity measurement unit in the diagnosis support system shown in FIG. 1.

FIG. 7 is a perspective view of the specimen preparation section 211, wherein the specimen preparation section 211 includes an L-shaped supporting plate 212, the fluid manifold 213, a syringe pump 214, and a stepping motor with reducer 215 are fixed on the supporting plate 212, as shown in the figure.

A screw shaft 216 is connected to the output shaft of the stepping motor 215. A drive arm 217 to be fit to the screw shaft 216 is connected to the distal end of a piston 218 of the syringe pump 214. The piston 218 moves up and down when the screw shaft 216 is rotated by the stepping motor 215. The syringe pump 214 and the fluid manifold 213 are connected to a liquid feeding tube 250 by way of connectors 219, 220. The syringe pump 214 is connected to a chamber 234 (see FIG. 10) accommodating fluid (washing liquid) for filling the flow channel by a liquid feeding tube 220b through a connector 220a.

Figure 8:
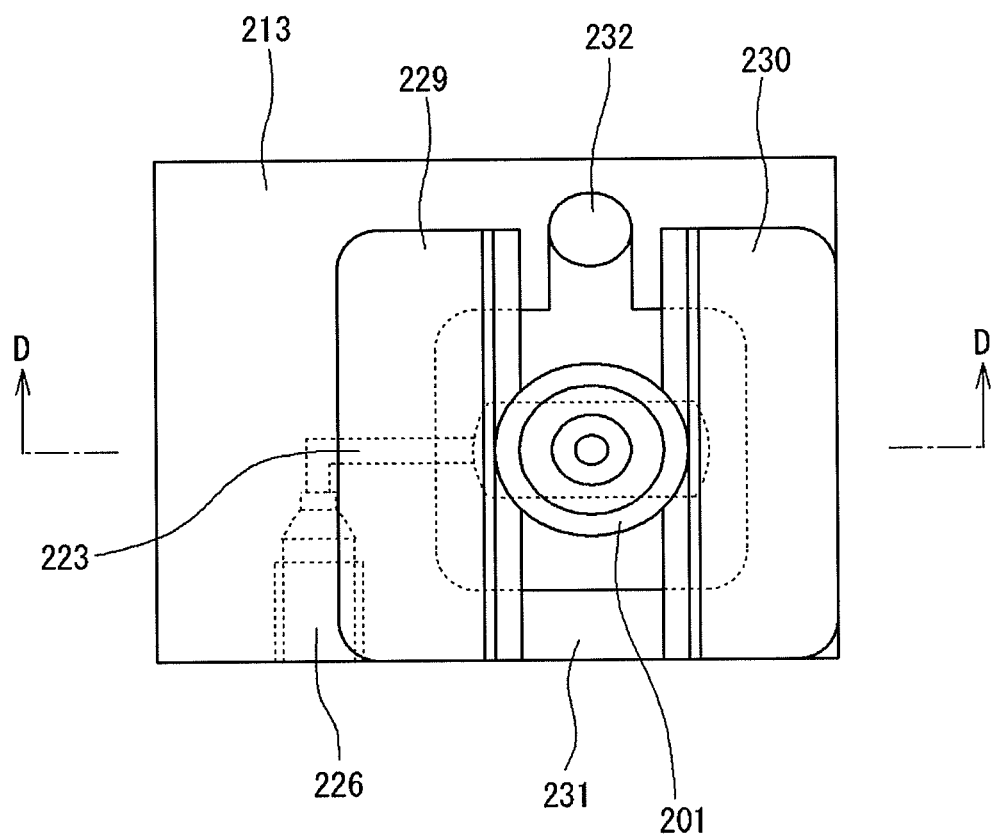
FIG. 8 is a top view of a fluid manifold of the specimen preparation section shown in FIG. 7.
Figure 9:
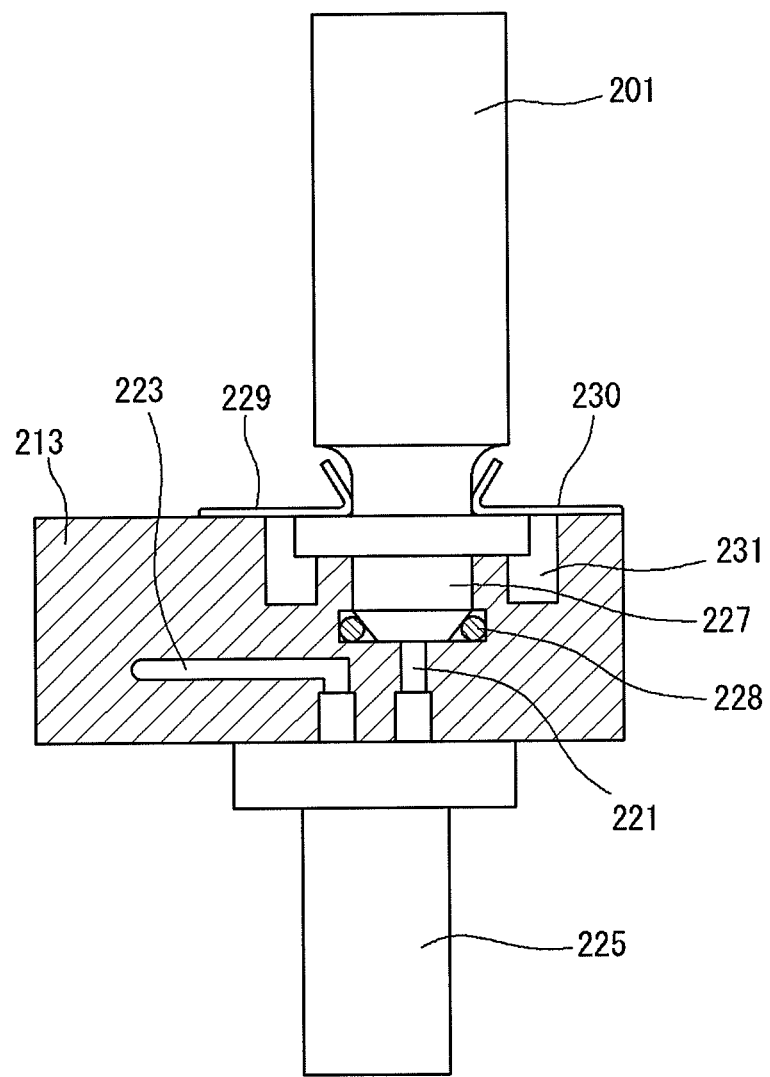
FIG. 9 is a cross sectional view taken along line D-D of FIG. 8.

As shown in FIGS. 8 and 9, the fluid manifold 213 includes a column connecting part 221 to which the lower opening of the column 201 is connected.

The fluid manifold 213 includes a flow channel 223 therein, and has an electromagnetic valve 225 for opening/closing the flow channel 223 and the column connecting part 221 on the lower surface. The fluid manifold 213 has on the side surface a connector connection screw hole 226 for connecting a connector 220, and this screw hole 226 is connected to the flow channel 223.

Figure 10:
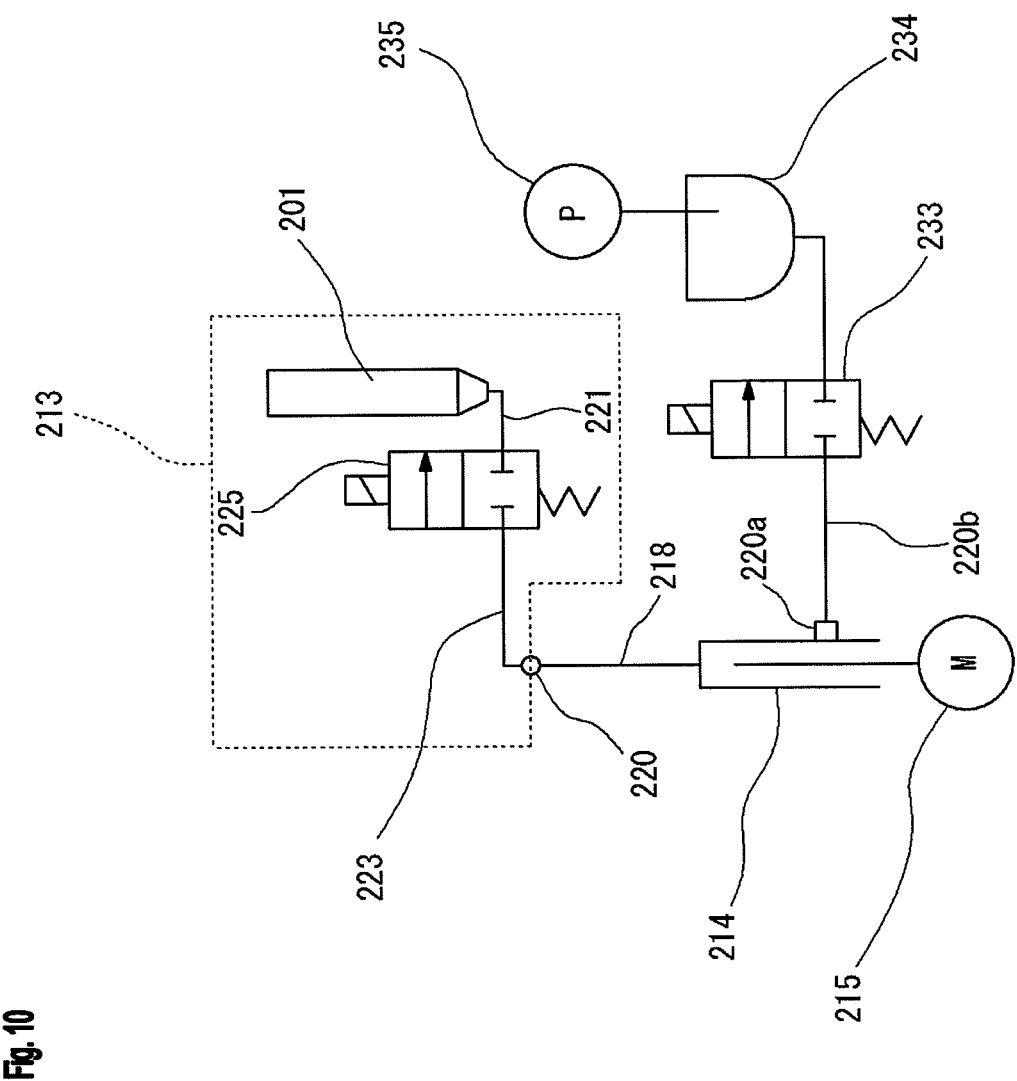
FIG. 10 is a fluid circuit diagram of the specimen preparation section shown in FIG. 7.

FIG. 10 is a fluid circuit diagram of the specimen preparation section 211, wherein a state in which the syringe pump 214 is connected to the fluid manifold 213 by way of the connector 220 is shown. A chamber 234 is connected to the syringe pump 214 by way of the electromagnetic valve 233, and positive pressure is applied to the chamber 234 from a positive pressure source 235.

A method of mounting the column 201 to the fluid manifold 213 will now be described.

As shown in FIGS. 8 to 10, a column mounting concave part 227 for receiving the lower end of the column 201 is formed on the upper surface of the fluid manifold 213, the center of the bottom part of the concave part 227 passes through the column connecting part 221, and an O-ring 228 is attached to the circumference of the bottom part. Two pressing plates 229, 230 having a cross section of L-shape are fixed in parallel on the upper surface of the fluid manifold 213 at an interval wider than the width W and narrower than D with the column mounting concave part 227 as a center.

In order to prevent sample or reagent that has passed the carrier 206 inside the column 201 fixed to the fluid manifold 213 from contacting fluid (washing liquid) that fills the flow channel 223 inside the fluid manifold 213 and being diluted, the electromagnetic valve 225 is opened (electromagnetic valve 233 is closed) before the column 201 is fixed to the column mounting concave part 227 and the syringe pump 214 is aspiration operated only by about 16 µL. The liquid level of the column connecting part 221 thereby lowers and an air gap forms.

Subsequently, the column 201 is mounted to the column mounting concave part 227 so that the flange 209 passes between the pressing plates 229, 230, and then rotated clockwise or counterclockwise by 90 degrees. The portion of the diameter D of the flange 209 engages the pressing plates 229, 230, and the flange 209 is fixed by the pressing plates 229, 230 due to the elasticity of the O-ring 228. When removing the column 201, the column 201 is rotated either to left or right by 90 degrees while being pushed.

When the column 201 is mounted to fluid manifold 213 of the specimen preparation unit 211, the concave part 227 of the fluid manifold 213 is filled with manually or automatically dispensed fluid in order to prevent air bubbles from being mixed, but when the distal end of the column 201 is inserted to the concave part 227, the fluid flows out due to increase in volume. An overflow storage concave part 231 is arranged at the periphery of the column mounting concave part 227 in order to prevent the fluid from flowing out to the periphery, and an overflow liquid discharging concave part 232 for aspirating and discharging the overflow liquid by pipette is arranged at one part of the overflow liquid storage concave part 231.

Various samples and reagents are injected or aspirated to or from a predetermined location by the dispensing mechanism section 3 equipped with the pipette.

The operation of the upper opening 205 of the column 201 in a case where the sample or the reagent is injected will now be described. The electromagnetic valve 225 is first opened (electromagnetic valve 233 is closed), and the syringe pump performs the aspirating operation when the sample or the reagent is injected to the opening 205. The air gap and the sample or the reagent are passed through the electromagnetic valve 225, and then aspirated to the syringe pump side. The syringe pump then performs ejecting operation. The sample or the reagent is then passed through the electromagnetic valve 225, and sent to the column 201.

[Dispensing Mechanism Section]

As shown in FIG. 1, the dispensing mechanism section 3 includes a frame 352 for moving the pipette in the X direction, a frame 353 for moving the pipette in the Y direction, and a plate 354 for moving the pipette in the Z direction.

The frame 352 includes a screw shaft 355 for moving the plate 354 in the direction of the arrow X, a guide bar 356 for supporting and slidably moving the plate 354, and a stepping motor 357 for rotating the screw shaft 355.

The frame 353 includes a screw shaft 358 for moving the plate 352 in the direction of the arrow Y, a guide bar 359 for supporting and slidably moving the frame 352, and a stepping motor 361 for rotating the screw shaft 358.

The plate 354 includes a screw shaft 367 for moving an arm 368 supporting the pipette 362 in the direction of the arrow Z, a guide bar for supporting and slidably moving the arm 368, and a stepping motor 370 for rotating the screw shaft 367.

In the present embodiment, since the dispensing mechanism section 3 is equipped with a pair of pipettes 362, reagent and the like can be simultaneously injected to two sample containers and content can be simultaneously aspirated from two sample containers, whereby the measuring process can be efficiently performed.

[Fluid Section]

As shown in FIG. 1, a fluid section 9 connected to the pipette washing bath 8 for washing the pipette 362 and each specimen preparation section 211, for operating the fluid is arranged at the rear part of the apparatus body 20. As shown in FIG. 10, the fluid section 9 includes an electromagnetic valve 225 of each specimen preparation section 211, an electromagnetic valve 233 for controlling the fluid when filling the liquid from the washing liquid chamber to the syringe 214, an electromagnetic valve for controlling fluid when aspirating and ejecting the liquid with the pipette 362, an electromagnetic valve for controlling the fluid when aspirating the liquid wasted from the pipette 362 in the waste bath 7, and an electromagnetic valve for controlling the fluid when washing the pipette 362 in the pipette washing bath 8.

[Detecting Section]

The detecting section 4 is provided to measure the fluorescence quantity based on the bound fluorescent labeled substance quantity reflecting the protein quantity and the fluorescence quantity based on the fluorescent labeled substance reflecting the amount of phosphate group, captured at the porous film 111 of the solid phase tip for protein 101, wherein excitation light is irradiated on the solid phase tip for protein 101, the generated fluorescence is detected, and the electric signal having a magnitude corresponding to the intensity of the detected fluorescence is output to the body controller 10. A generally used detecting section configured by light source unit, illumination system, and light receiving system is appropriately adopted for the detecting section 4.

[Data Processing Unit]

Figure 11:
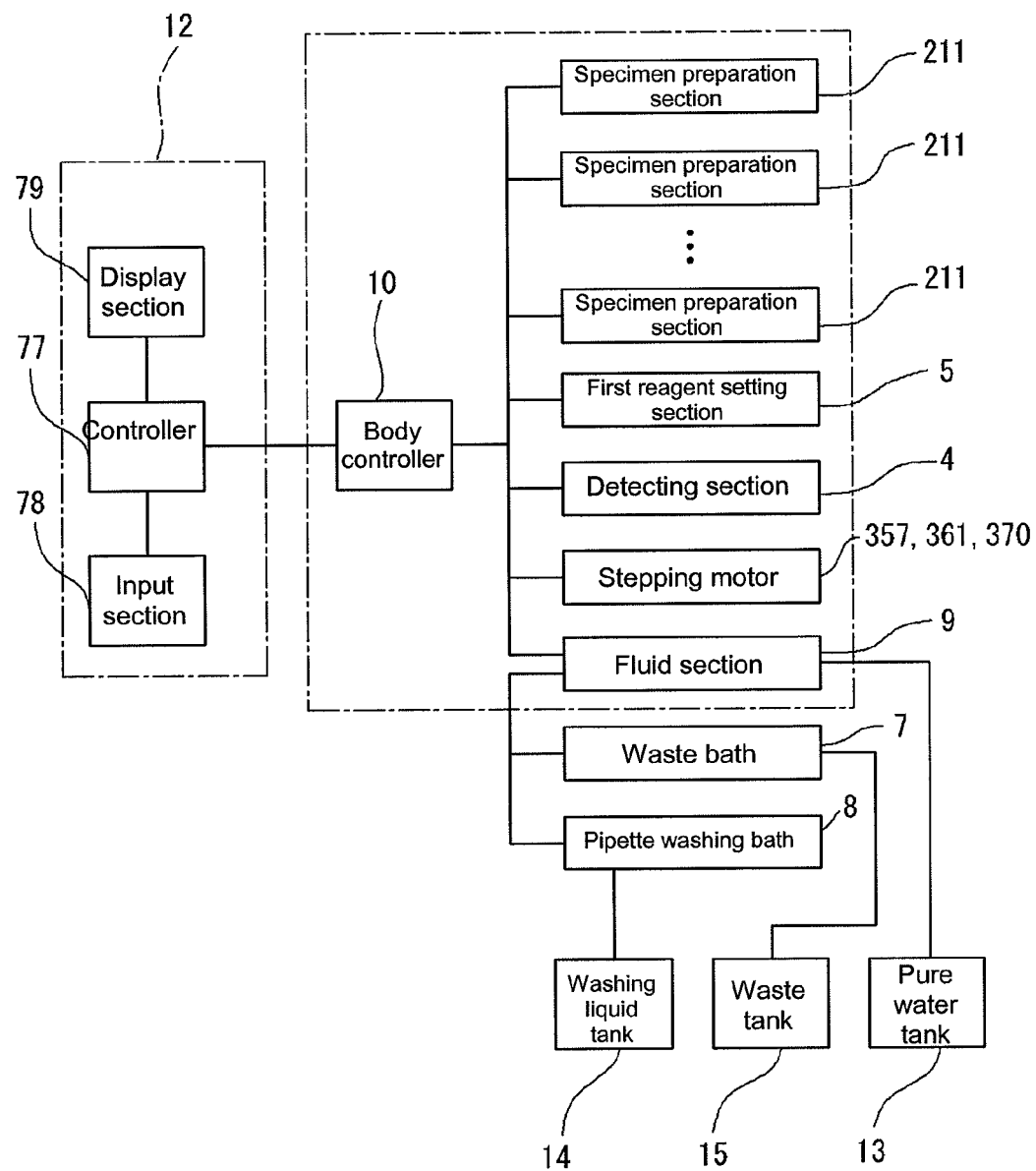
FIG. 11 is a block diagram showing a partial configuration of the diagnosis support system (control system for controlling diagnosis support system)

FIG. 11 is a block diagram showing a partial configuration (control system for controlling the diagnosis support system) of the diagnosis support system of the present embodiment. As shown in FIG. 11, the data processing unit 12 or the personal computer includes a controller 77, an input section 78, and a display section 79.

The controller 77 has a function of transmitting an operation start signal of the apparatus to the body controller 10 to be hereinafter described. When a command to start operation is transmitted from the controller 77, the body controller 10 outputs a drive signal for driving the stepping motor 215 of each specimen preparation section 211, a drive signal for adjusting the temperature of the first reagent setting section 5, a drive signal for driving the stepping motors 357, 361, 370, and a drive signal for driving the electromagnetic valve in the fluid section 9. The controller 77 also has a function of analyzing the detection result obtained in the detecting section 4. The detection result obtained in the detecting section 4 is transmitted to the body controller 10. The body controller 10 transmits the detection result obtained in the detecting section 4 to the controller 77.

The display section 79 is arranged to display result of analysis and the like obtained in the controller 77.

Figure 12:
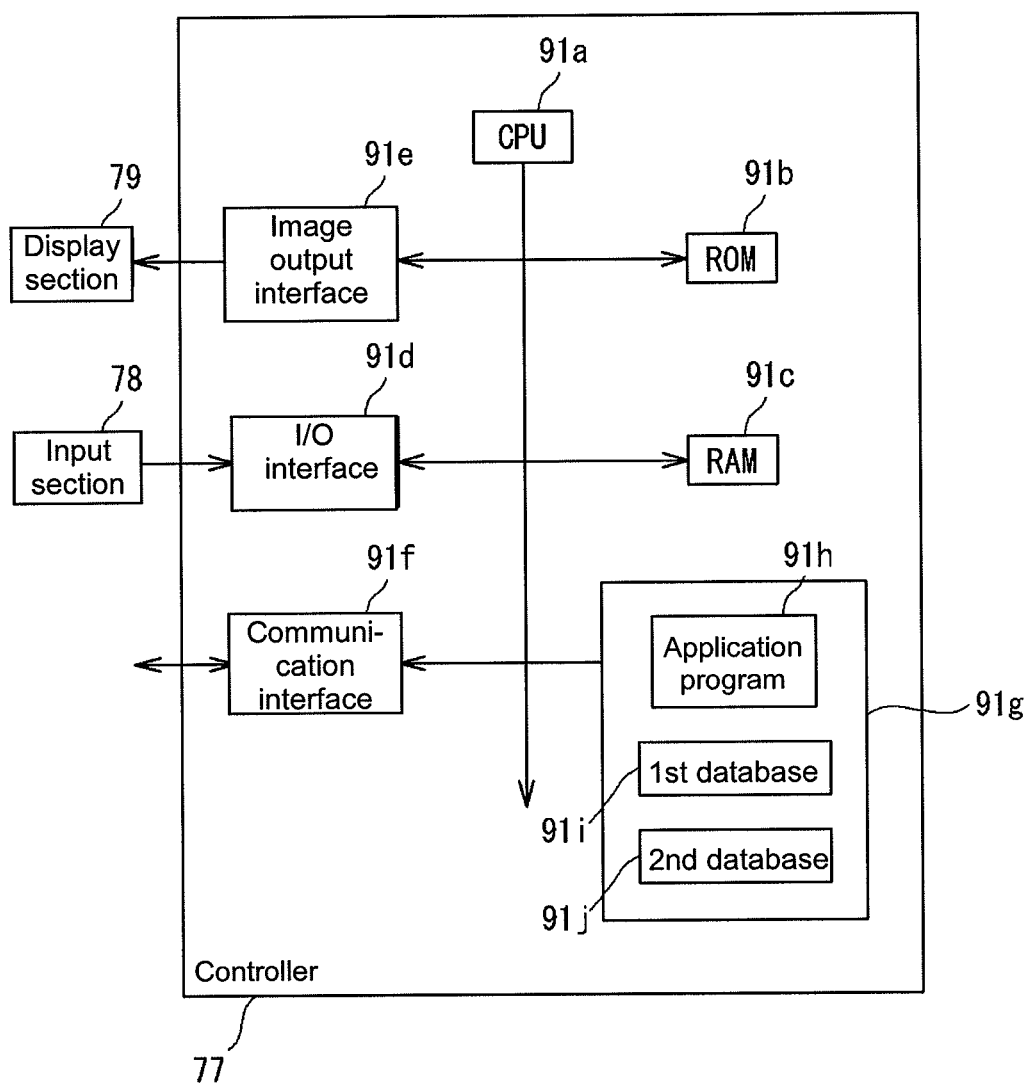
FIG. 12 is a block diagram showing a hardware configuration of a data processing unit.

The configuration of the personal computer used as the data processing unit 12 will now be described in detail. As shown in FIG. 12, the controller 77 is mainly configured by a CPU 91a, a ROM 91b, a RAM 91c, an input/output interface 91d, an image output interface 91e, a communication interface 91f, and a hard disc 91g. The CPU 91a, the ROM 91b, the RAM 91c, the input/output interface 91d, the image output interface 91e, the communication interface 91f, and the hard disc 91g are connected with an electric signal line (bus) so as to communicate electrical signals.

The CPU 91a executes computer programs stored in the ROM 91b and the computer programs loaded in the RAM 91c. The personal computer serves as the data processing unit 12 when the CPU 91a executes the application program 91h to be hereinafter described, and executes the operations to be hereinafter described.

The ROM 91b is configured by mask ROM, PROM, EPROM, EEPROM, and the like, and is recorded with computer programs to be executed by the CPU 91a, data used for the same, and the like.

The RAM 91c is configured by SRAM, DRAM, and the like. The RAM 91c is used to read out the computer programs recorded on the ROM 91b and the hard disc 91g. The RAM 91c is used as a work region of the CPU 91a when executing the computer programs.

The hard disc 91g is installed with various computer programs to be executed by the CPU 91a such as operating system and application program, as well as data used in executing the computer program. The application program 91h for acquiring the expression levels and the activity values of the CDK1 and the CDK2, calculating the CDK1 specific activity and the CDK2 specific activity from the acquired expression levels and the activity values of the CDK1 and the CDK2, determining a reference range based on the calculated CDK1 specific activity and the CDK2 specific activity, specifying sample data of other cancer patients having the CDK1 specific activity and the CDK2 specific activity within the determined reference range, calculating the recurrence rate based on the specified sample data, determining the risk of recurrence based on the calculated recurrence rate, generating a screen including the result of the calculated recurrence rate and the determination result of the recurrence risk, and displaying the generated screen on the display section 79 is also installed in the hard disc 91g.

In order to acquire the expression level and the activity value, the hard disc 91g includes a first database 91i for storing a standard curve or conversion data for converting fluorescence intensity to expression level or activity value. The standard curve may be obtained for every measurement of the expression level or the activity value. The first database 91i of the hard disc 91g stores data to use for the calculation for determining the reference range, data of default value of the reference range, and data of the set value of the reference range input and used in the past. The first database 91i of the hard disc 91g stores a reference value for determining the recurrence risk by being compared with the calculated recurrence rate.

The hard disc 91g includes a second database 91j for storing sample data in which the measurement value such as the activity value and the expression level of the cancer patient and the clinical information such as presence/absence of recurrence, information related to postsurgical treatment, information related to living body and the like of the patient are corresponded to each other.

Operating system providing graphical user interface environment such as Windows (registered trademark) manufactured and sold by US Microsoft Co. is installed in the hard disc 91g. In the following description, the application program 91h according to the present embodiment is assumed to operate on the operating system.

The input/output interface 91d is configured by serial interface such as USB, IEEE1394, RS-232C; parallel interface such as SCSI, IDE, IEEE1284; analog interface such as D/A converter, A/D converter, and the like. The input section 78 is connected to the input/output interface 91d, so that the user can input data to the data processing unit 12 by using the input section 78.

The communication interface 91f is, for example, Ethernet (registered trademark) interface. The data processing unit 12 transmits and receives data with the body controller 10 by using a predetermined communication protocol by means of the communication interface 91f.

The image output interface 91e is connected to the display section 79 configured by LCD, CRT, or the like, and is configured to output an image signal corresponding to the image data provided from the CPU 91a to the display section 79. The display section 79 displays the image (screen) according to the input image signal.

[Body Controller]

The body controller 10 connected to each specimen preparation section 211, the detecting section 4, the stepping motors 357, 361, 370, the fluid section 9 and the like, for controlling the same is arranged at a back part of the apparatus body 20.

Figure 13:
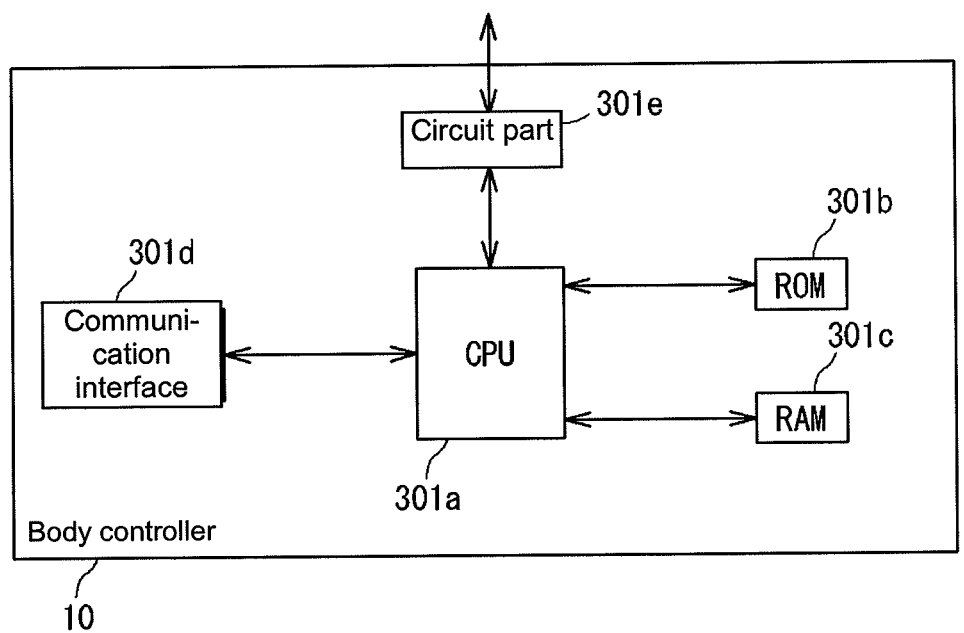
FIG. 13 is a block diagram showing a hardware configuration of a body controller.

As shown in FIG. 13, the body controller 10 includes a CPU 301a, a ROM 301b, a RAM 301c, a communication interface 301d, and a circuit part 301e.

The CPU 301a can execute computer programs stored in the ROM 301b and the computer programs loaded in the RAM 301c.

The ROM 301b stores a computer program to be executed by the CPU 301a, data used in the execution of the computer program, and the like.

The RAM 301c is used in reading out the computer program stored in the ROM 301b. The RAM 301c is used as a work region of the CPU 301a when executing the computer programs.

The communication interface 301d is, for example, Ethernet (registered trademark) interface. The body controller 10 transmits and receives data with the data processing unit 12 by using a predetermined communication protocol by means of the communication interface 301d.

The circuit part 301e includes a plurality of drive circuits and a signal processing circuit (not shown). The drive circuit is arranged in correspondence to the specimen preparation section 211, the first reagent setting section 5, the detecting section 4, the stepping motors 357, 361, 370, and the fluid section 9. Each drive circuit generates a control signal (drive signal) for controlling the corresponding unit (specimen preparation section 211 if being drive circuit corresponding to the specimen preparation section 211) according to the instruction data provided from the CPU 301a, and transmits the control signal to the unit. The output signal of the sensor arranged in the unit is provided to the drive circuit, wherein the drive circuit converts the output signal to a digital signal and provides the same to the CPU 301a. The CPU 301a generates the instruction data based on the provided output signal of the sensor.

The signal processing circuit is connected to the detecting section 4. A detection signal indicating fluorescence intensity is output from the detecting section 4, and such detection signal is provided to the signal processing circuit. The signal processing circuit executes signal processing such as noise removal process, amplification process, and A/D conversion process on the detection signal. The data on the detection result obtained as a result of the signal processing is provided to the CPU 301a.

[3] Diagnosis Support of Cancer

The operation of the diagnosis support system according to the present embodiment will be described.

(1) Pre-Process by Solubilizing Device B

Prior to the process by the measuring device A, liquid sample is collected from the tissue containing the malignant tumor resected from a cancer patient by using the solubilizing device B. In a procedure, the tissue is first placed in a container by using a pin set. The container is then set in the sample setting section 33 of the solubilizing device B shown in FIG. 1, and the start button of the operating section 31 is pushed, whereby the pestle 34 lowers to a predetermined position and pushes the tissue in the container against the bottom of the container.

Solubilizing liquid (buffer solution containing surfactant and proteolysis enzyme inhibiting agent, and the like) is automatically or manually injected into the container in such state. Thereafter, the tissue is grinded by the rotation of the pestle 34. The drive of the pestle 34 is stopped after a predetermined time has elapsed, the pestle 34 is moved upward, and thereafter, the container is taken out from the sample setting section 33. The solubilized content in the container is then set in the centrifugal machine, and the obtained supernatant solution is manually collected as a sample.

(2) Setting of Sample and the Like to the Measuring Device A

The supernatant solution is placed in two sample containers and diluted at dilution ratio different from each other, and thereafter, the sample containers are set at predetermined positions in the first reagent setting section 5. Of two samples, one is the sample for expression level measurement, and the other is the sample for activity value measurement.

The solid phase tip for protein 101 is set in the tip setting section 1, and eight columns 201 are respectively set in the specimen preparation section 211 of the activity measurement unit 2.

(3) Overall Flow of Process by Diagnosis Support System

FIGS. 15 to 20 show overall flow of the process by the diagnosis support system. In the judgment in the following flowchart, down refers to Yes and right (left) refers to No unless specifically written as "Yes" and "No". The processes described below are processes controlled by the controller 77 and the body controller 10.

When the power of the apparatus body 20 is turned ON, initialization of the body controller 10 is performed (step S1). In this initialization operation, initialization of the program, return to an origin position for the driving section of the apparatus body 20, and the like are performed.

When the power of the data processing unit 12 or the personal computer is turned ON, initialization of the controller 77 is performed (step S201). In this initialization operation, initialization of the program, or the like is performed. After the initialization is completed, a menu screen (not shown) including an input screen display button for instructing the display of an input screen is displayed on the display section 79. The user operates the input section 78 to select the input screen button for instructing the display of the input screen of the menu screen.

In step S202, the controller 77 of the data processing unit 12 determines whether or not the input screen is being displayed. The controller 77 advances the process to step S205 when determining that the input screen is being displayed (Yes), and advances the process to step S203 when determining that the input screen is not being displayed (No).

In step S203, the controller 77 determines whether or not a display instruction of the input screen has been made (that is, whether or not input screen button for instructing the display of the input screen of the menu screen is selected). The controller 77 advances the process to step S204 when determining that the display instruction of the input screen has been made (Yes), and advances the process to step S301 when determining that the display instruction of the input screen has not been made (No).

In step S204, the controller 77 of the data processing unit 12 displays the input screen on the display section 79.

In step S205, the user operates the input section 78 to input sample information such as ID number and age of the subject cancer patient. Thereafter, in step S206, the information input with the input section 78 are stored in the hard disc 91h. The instruction to start the measurement is made with the user operating the input section 78 of the personal computer 12 and selecting a start button displayed on the input screen.

In step S207, the controller 77 determines whether or not the instruction to start the measurement is made. The controller 77 advances the process to step S208 when determining that the instruction to start the measurement is made (Yes), and advances the process to step S301 when determining that the instruction to start the measurement is not made (No). In step S208, a measurement start signal is transmitted from the controller 77 to the body controller 10.

In step S2, the body controller 10 determines whether or not the measurement start signal is received. The body controller 10 advances the process to step S3 when determining that the measurement start signal is received (Yes), and advances the process to step S8 when determining that the measurement start signal is not received (No).

In step S3, the process to prepare the specimen for expression level measurement is performed. The sample is aspirated from the sample container set in the first reagent setting section 5. A predetermined process is performed on the aspirated sample, and the specimen for expression level measurement is prepared.

In step S4, the process to prepare the specimen for activity value measurement is performed. The sample is aspirated from the sample container set in the first reagent setting section 5. A predetermined process is performed on the aspirated sample, and the specimen for activity value measurement is prepared.

In step S5, the tip setting section 1 set with the solid phase tip for protein 101 including the specimen for expression level measurement and the specimen for activity value measurement is moved into the detecting section 4 from the position shown in FIG. 1.

In step S6, excitation light is irradiated on each well of the solid phase tip for protein 101, and fluorescence radiated from each specimen is detected.

In step S7, the detected detection result is transmitted from the body controller 10 to the controller 77 of the personal computer 12.

In step S209, the controller 77 determines whether or not the detection result is received. The controller 77 advances the process to step S210 when determining that the detection result is received (Yes). The controller 77 again executes the process of step S209 when determining that the detection result is not received (No).

In step S210, the controller 77 executes an analyzing process from the acquired detection result.

In step S211, the controller 77 displays the result of analysis such as the result of the recurrence rate calculated in step S210 and the result of the determined recurrence risk on the display section 79.

Figure 21:
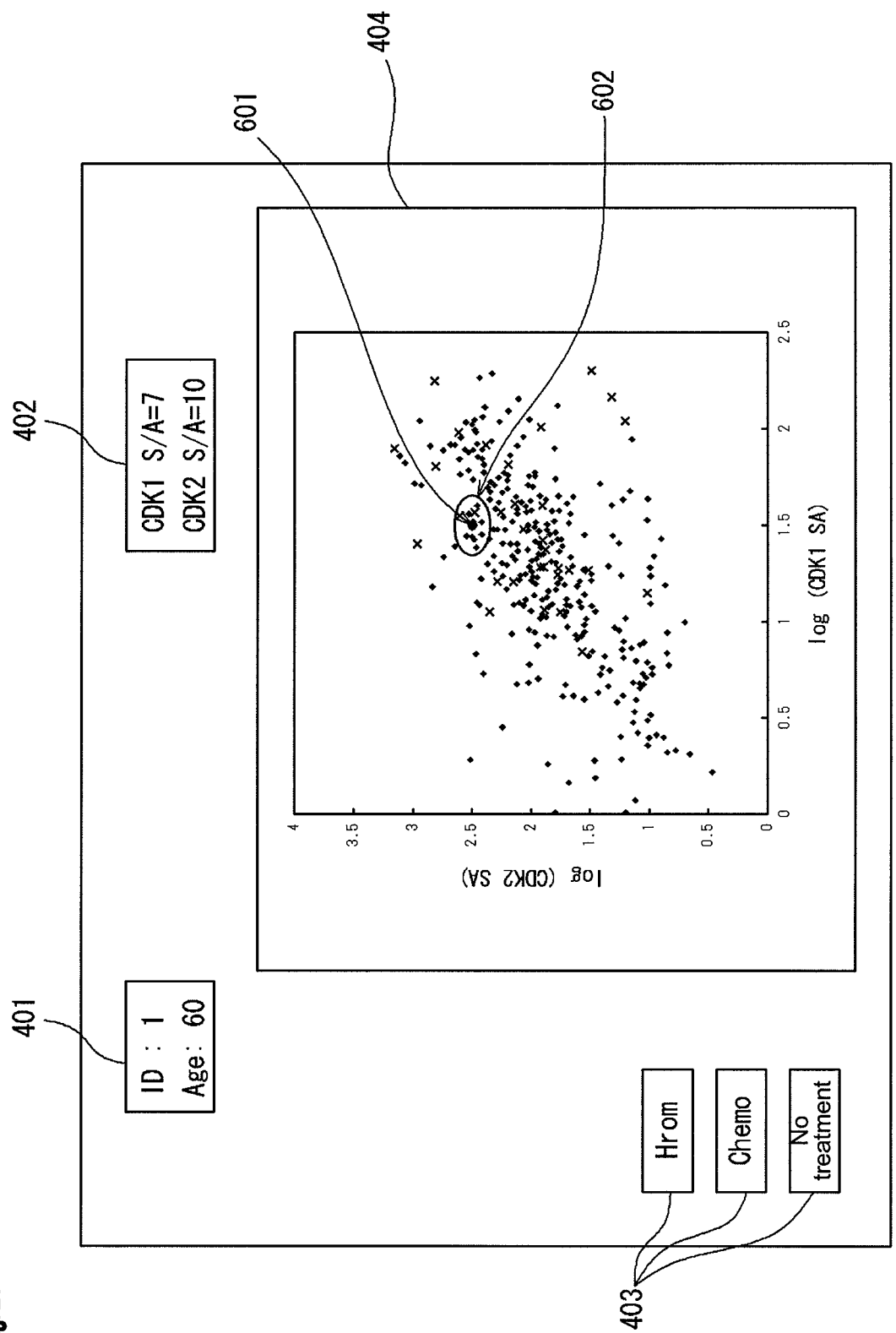
FIG. 21 is a view showing an example of a display screen of diagnosis support information.
Figure 22:
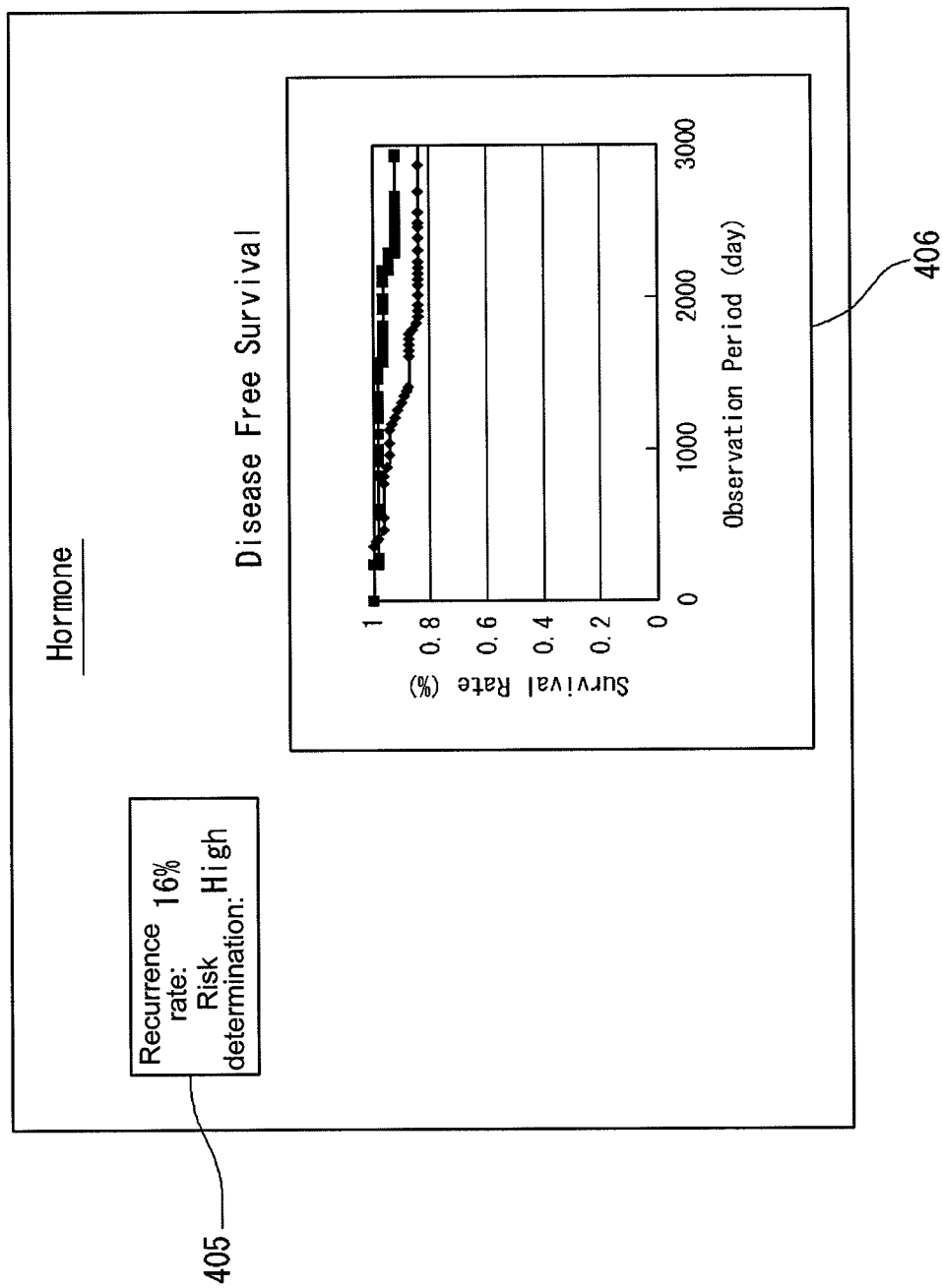
FIG. 22 is a view showing an example of a display screen of diagnosis support information.

FIGS. 21 and 22 show one example of a display screen of the diagnosis support information.

In the display screen shown in FIG. 21, ID number, age, and the like of the cancer patient to be diagnoses are displayed on a display section 401. The CDK1 specific activity value and the CDK2 specific activity value are displayed on an information display section 402 as a measurement value of a predetermined measurement item related to the malignant tumor of the cancer patient to be diagnosed. A display button icon 403 is a display button icon for moving to the display screen (FIG. 22) of the information every treatment group after resection of malignant tumor such as no treatment, hormone therapy and chemotherapy. The display screen (FIG. 22) of information every treatment group after resection of malignant tumor is displayed as a window different from the window displaying the screen of FIG. 21 when the user pushes the display button icon 403. The screen of FIG. 21 may be switched to the screen of FIG. 22 and displayed instead of being displayed as separate windows. The distribution diagram of the CDK1 specific activity value and the CDK2 specific activity value is displayed on a distribution diagram display section 404 as the measurement value of the predetermined measurement item related to the malignant tumor of other cancer patients. The points corresponding to the CDK1 specific activity value and the CDK2 specific activity value of the malignant tumor of the cancer patient to be diagnosed are drawn on the distribution diagram. In the distribution diagram, the reference range 602 determined based on the measurement value 601 (CDK1 specific activity value and the CDK2 specific activity value of the malignant tumor) of the subject cancer patient is drawn.

In the display screen shown in FIG. 21, a three-dimensional distribution diagram may be displayed in the distribution diagram display section 404 instead of the two-dimensional distribution diagram of the CDK1 specific activity value and the CDK2 specific activity value. In this case, other parameters become the coordinate axis in addition to the CDK1 specific activity value and the CDK2 specific activity value.

FIG. 22 shows one example of the display screen of information on the hormone therapy group after resection of malignant tumor. Information such as recurrence rate, and recurrence risk are displayed on the information display section 405.

According to the diagnosis support system of the present embodiment, the recurrence rate is calculated based on the information on the presence/absence of recurrence of other cancer patients indicating an approximate specific activity. The calculated recurrence rate can be indicated as an expected recurrence rate of the cancer patient to be diagnosed. Therefore, the user can obtain diagnosis support information with higher precision by the diagnosis support system of the present embodiment. Information such as disease free survival is displayed on the information display section 406.

In step S301, the controller 77 determines whether or not an input screen of the set values such as the reference value for determining the recurrence risk, and the value (radius) for determining the reference range is being displayed. The controller 77 advances the process to step S305 when determining that the input screen of the set value is being displayed (Yes), and advances the process to step S302 when determining that the input screen of the set value is not being displayed (No).

In step S302, the controller 77 determines whether or not a display instruction of the input screen of the set value is made. The controller 77 advances the process to step S303 when determining that the display instruction of the input screen of the set value is made (Yes), and advances the process to step S307 when determining that the display instruction of the input screen of the set value is not made (No).

In step S303, the RAM 91g of the controller 77 reads out data such as the reference value for determining the recurrence risk and the value (radius) for determining the reference range stored in the first database 91i of the hard disc 91g.

In step S304, the input screen of the set value is displayed on the display section 79 by the controller 79. New values are input for the set values such as the reference value and the value (radius) for determining the reference range with the user operating the input section 78.

In step S305, the controller 77 determines whether or not the input of the set value is made. The controller 77 advances the process to step S306 when determining that the input of the set value is made (Yes), and advances the process to step S307 when determining that the input of the set value is not made (No).

In step S306, the input new set value is stored in the first database 91i of the hard disc 91g.

In step S307, the controller 77 determines whether or not an instruction to shutdown is accepted. The controller 77 advances the process to step S308 when determining that the instruction to shutdown is accepted (Yes), and returns the process to step S202 when determining that the instruction to shutdown is not accepted (No). In step S308, a shutdown signal is transmitted from the controller 77 to the body controller 10. In step S309, the controller 77 performs the process of shutting down the personal computer 12, and completes the process.

In step S8, the body controller 10 determines whether or not the shutdown signal has been received. The body controller 10 advances the process to step S9 when determining that the shutdown signal has been received (Yes), and returns the process to step S2 when determining that the shutdown signal has not been received (No). In step S9, the body controller 10 shuts down the apparatus body 20, and terminates the process.

(4) Preparation Process of Expression Level Measurement Specimen

Figure 17:
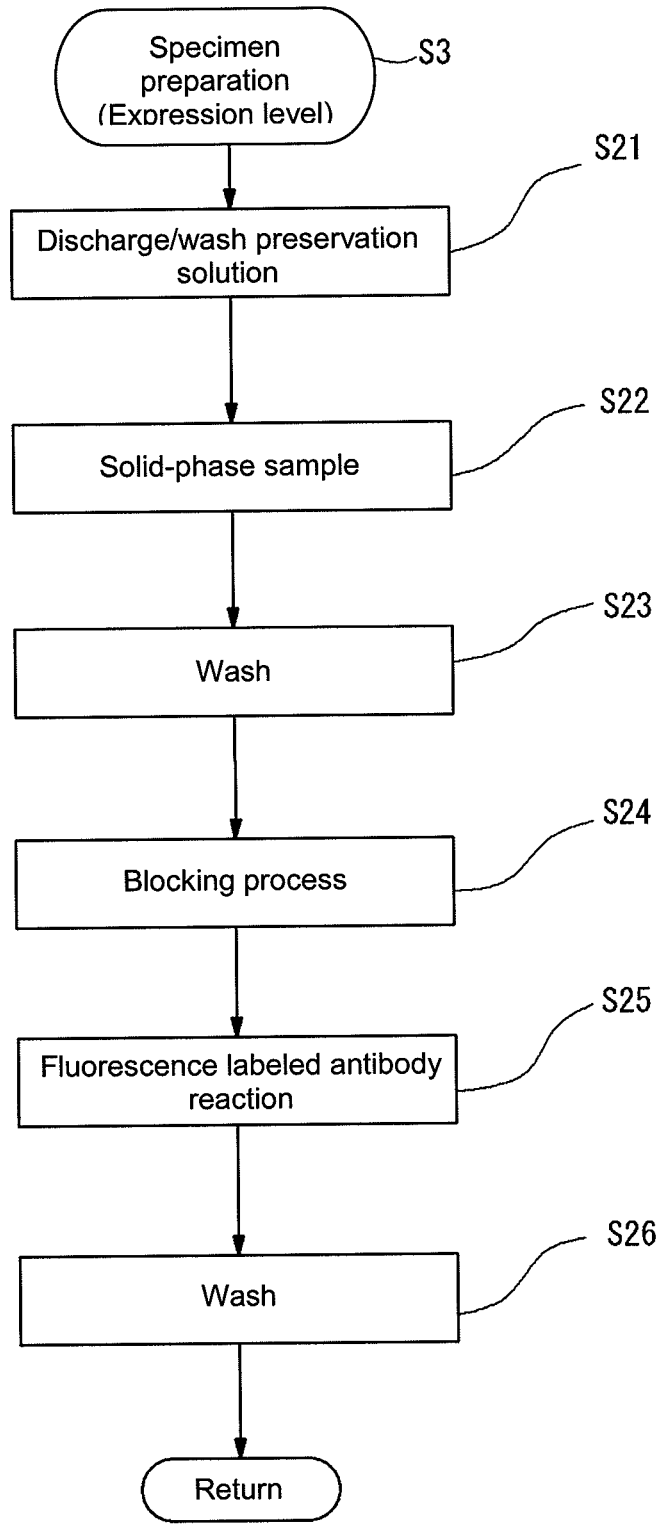
FIG. 17 is a view showing a flow of one example of a preparation process of the expression level measurement sample.

The flow of one example of the preparation process of the expression level measurement specimen in step S3 is shown in FIG. 17.

First, in step S21, the preservation solution stored in advance in each well of the solid phase tip for protein is discharged, and the inside of each well is washed. The washing is performed by injecting washing liquid to each well from the upper side through the pipette of the dispensing mechanism section 3, and aspirating the injected washing liquid through the porous film by negative pressure from the lower side of the solid phase tip for protein. The following washing step is similarly carried out.

The sample for the expression level measurement is aspirated by the pipette from the sample container set in the first reagent setting section 5, and the resulting sample is injected to a plurality of predetermined wells, and is aspirated by negative pressure from the lower side of the solid phase tip for protein. The protein is solid-phased at the porous film of the solid phase tip for protein (step S22).

Similar to step S21, the inside of the predetermined well is washed with the washing liquid. Accordingly, the components other than the protein are removed from the porous film of the solid phase tip for protein (step S23).

Subsequently, the blocking liquid is injected to the predetermined well, and the blocking liquid remaining in the well after leaving for 15 minutes or longer (e.g., for 30 minutes) is discharged (step S24). Accordingly, the fluorescence labeled CDK1 antibody (fluorescence labeled CDK1 antibody) and the fluorescence labeled CDK2 antibody (fluorescence labeled CDK2 antibody) are prevented from being solid-phased at the site of the porous film where the protein is not solid-phased. The commercially available fluorescence labeled CDK1 antibody and the fluorescence labeled CDK2 antibody may be used.

The fluorescence labeled CDK1 antibody and the fluorescence labeled CDK2 antibody are respectively injected to the predetermined well. In this case, each fluorescence labeled antibody is injected into two wells. The injected fluorescence label is discharged after 20 to 30 minutes have elapsed and the reaction of the fluorescence labeled antibody and the protein (CDK1 or CDK2) solid-phased on the porous film is terminated (step S25).

Finally, similar to step S23, the inside of the predetermined well is washed with the washing liquid (Step S26). The body controller 10 then returns the process to step S4 of the main routine shown in FIG. 15.

(5) Preparation Process of Activity Value Measurement Specimen

Figure 18:
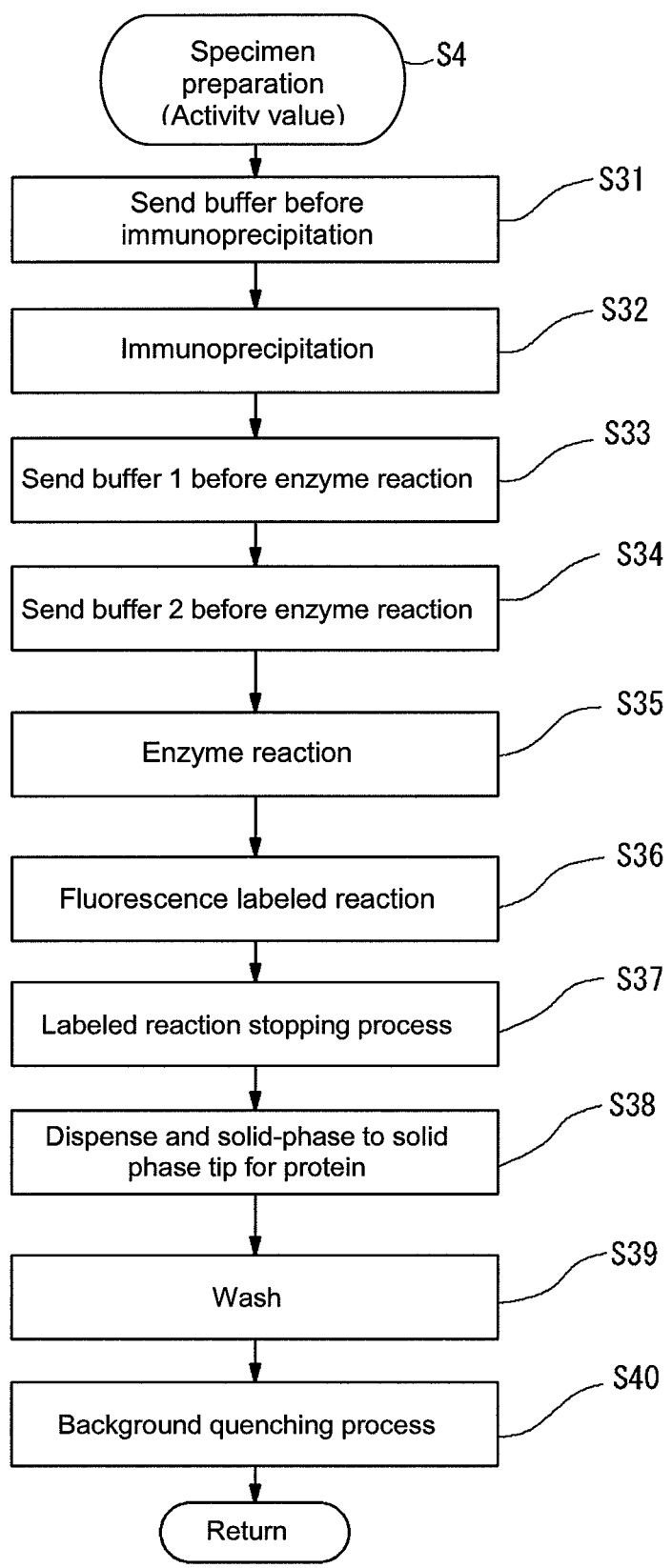
FIG. 18 is a view showing a flow of one example of a preparation process of the activity value measurement sample.

FIG. 18 shows a flow of the preparation process of the activity value measurement specimen in step S4. In the preparation process of the activity value measurement specimen, four specimen preparation sections 211 are arranged on the near side in the figure and four specimen preparation sections 211 are arranged on the far side in the figure as the activity measurement unit 2 shown in FIG. 1. Each specimen preparation section 211 of the activity measurement unit 2 includes a first specimen preparation section (Ac1), a second specimen preparation section (Ac2), a third specimen preparation section (Ac3), and a fourth specimen preparation section (Ac4), from the left on the far side of the figure, and a fifth specimen preparation section (Ac5), a sixth specimen preparation section (Ac6), a seventh specimen preparation section (Ac7), and an eighth specimen preparation section (Ac8), from the left on the near side of the figure.

For each of the first to the eighth specimen preparation sections (Ac1 to Ac 8), a buffer or a washing reagent is injected to the opening 205 with the pipette of the dispensing mechanism section 3. For each of the first to the eighth specimen preparation sections (Ac1 to Ac8), the syringe pump 214 and the electromagnetic valve 225 operate as described above, so that the buffer of the liquid storage section 204 passes through the carrier 206 into the flow channel 223, and again passes through the carrier 206 and returns to the liquid storage section 204. The buffer returned to the liquid storage section 204 in all the columns 201 is aspirated and discarded with the pipette of the dispensing mechanism section 3 (step S31).

Immunoprecipitation (reaction between antibody and CDK) is then performed (step S32). First, the sample 1 for the activity value measurement is aspirated by one pipette and the sample 2 for the activity value measurement is aspirated by another pipette from one sample container set in the first reagent setting section 5.

Figure 23:
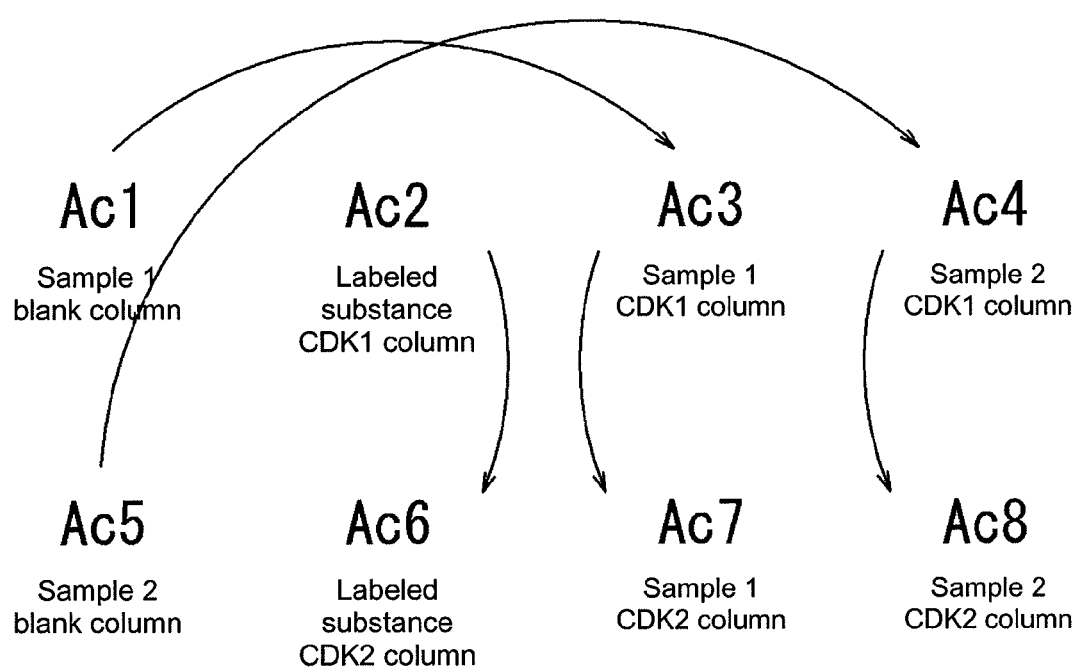
FIG. 23 is an explanatory view showing the usage procedures of the sample and the like in the diagnosis support system.

As shown in FIG. 23, the sample 1 for the activity value measurement aspirated from the sample container is first injected to the liquid storage section 204 of the first specimen preparation section (Ac1). The sample 1 is sent to the carrier 206 of the first specimen preparation section (Ac1) by operating the syringe pump 214 and the electromagnetic valve 225 as described above. In this case, the sample 1 reciprocates in the carrier 206 of the column 201 once by reciprocating the piston 218 up and down once (aspiration→discharge).

The sample 2 for activity value measurement aspirated from the sample container is first injected to the liquid storage section 204 of the fifth specimen preparation section (Ac 5). The sample 2 is similarly sent to the carrier 206 of the fifth specimen preparation section (Ac 5).

The antibody of the CDK1 nor the antibody of the CDK2 are immobilized on the carrier 206 of the columns 201 of the first specimen preparation section (Ac1) and the fifth specimen preparation section (Ac5). Therefore, the CDK1 and the CDK2 are not solid-phased in the first specimen preparation section (Ac1) and the fifth specimen preparation section (Ac5), the sample 1 containing the CDK1 and the CDK2 is stored in the column 201 of the first specimen preparation section (Ac1), and the sample 2 containing the CDK1 and the CDK2 is stored in the column 201 of the fifth specimen preparation section (Ac5).

The sample 1 stored in the column 201 of the first specimen preparation section (Ac1) is then aspirated by the pipette, and injected to the liquid storage section 204 of the third specimen preparation section (Ac3). The sample 1 is then sent to the carrier 206 of the third specimen preparation section (Ac3), similar to the above.

The sample 2 stored in the column 201 of the fifth sample specimen section (Ac5) is aspirated by the pipette, and injected to the liquid storage section 204 of the fourth specimen preparation section (Ac4). The sample 2 is then sent to the carrier 206 of the fourth specimen preparation section (Ac4), similar to the above.

The antibody of the CDK1 is immobilized to the carriers 206 of the columns 201 of the third specimen preparation section (Ac3) and the fourth specimen preparation section (Ac4). Therefore, the CDK1 is solid-phased but the CDK2 is not solid-phased in the third specimen preparation section (Ac3) and the fourth specimen preparation section (Ac4), the sample 1 not containing the CDK1 but containing the CDK2 is stored in the column 201 of the third specimen preparation section (Ac3), and the sample 2 not containing the CDK1 but containing the CDK2 is stored in the column 201 of the fourth specimen preparation section (Ac4).

The sample 1 stored in the column 201 of the third specimen preparation section (Ac3) is then aspirated by the pipette, and injected to the liquid storage section 204 of the seventh specimen preparation section (Ac7). The sample 1 is then sent to the carrier 206 of the seventh specimen preparation section (Ac7), similar to the above.

The sample 2 stored in the column 201 of the fourth specimen preparation section (Ac4) is aspirated by the pipette, and injected to the liquid storage section 204 of the eighth specimen preparation section (Ac8). The sample 2 is then sent to the carrier 206 of the eighth specimen preparation section (Ac8), similar to the above.

The antibody of the CDK2 is immobilized to the carrier 206 of the columns 201 of the seventh specimen preparation section (Ac7) and the eighth specimen preparation section (Ac8). Therefore, the CDK2 is solid-phased in the seventh specimen preparation section (Ac7) and the eighth specimen preparation section (Ac8), and thus the sample 1 neither containing the CDK1 nor the CDK2 is stored in the column 201 of the seventh specimen preparation section (Ac7), and the sample 2 neither containing the CDK1 nor the CDK2 is stored in the column 201 of the eighth specimen preparation section (Ac8).

The sample 1 and the sample 2 stored in the columns 201 of the seventh specimen preparation section (Ac7) and the eighth specimen preparation section (Ac8) are respectively aspirated by the pipette, and disposed in the waste bath 7.

The first specimen preparation section (Ac1) and the fifth specimen preparation section (Ac5) are used for activity measurement of the background, the third specimen preparation section (Ac3) and the fourth specimen preparation section (Ac4) are used for activity measurement of the CDK1, and the seventh specimen preparation section (Ac7) and the eighth specimen preparation section (Ac8) are used for activity measurement of the CDK2.

Therefore, by injecting the specimen remaining in the column into another column, the background activity measurement, the CDK1 activity measurement, and the CDK2 activity measurement can be performed with small amount of sample.

The buffer 1 is then sent to the columns 201 to wash and remove unnecessary components in the sample (step S33).

Subsequently, since the buffer 1 influences enzyme reaction executed in step S25, the buffer 2 is sent to the column 201 to wash off the components of the buffer 1 for the main purpose of creating a condition for the relevant enzyme reaction (step S34).

The substrate reaction solution containing substrate Histon H1 and ATPγS is then injected to the column 201, and the piston 219 is reciprocated once (step S35). The liquid pushed out from the lower side of the column 201 is stored in the column 201 as it is. According to such step, the phosphate group is introduced to the Histon H1 with the CDK1 and the CDK2 as enzymes. The amount of phosphate group is influenced by the strength (i.e., activity value) of the work of the CDK1 or the CDK2 as enzyme, and thus the activity value of the CDK1 or the CDK2 can be obtained by measuring the amount of phosphate group. The background activity value obtained using the first specimen preparation section (Ac1) and the fifth specimen preparation section (Ac5) shown in FIG. 23 is used to perform background correction as hereinafter described.

The fluorescent labeled reagent is dispensed directly into the column 201 from above the column 201 by using the pipette to bind the fluorescent labeled substance to the phosphate group introduced into the Histon H1 (step S36). In this case, the pipette repeats aspiration and discharge of liquid in the column for a predetermined time to stir the liquid in the column 201.

A reaction stopping solution is directly dispensed to the column 201 similar to the fluorescent labeled reagent after a predetermined time (e.g., for twenty minutes) has elapsed from the start of step S26. The liquid in the column 201 is stirred by repeating aspiration and discharge of the liquid in the column for a predetermined time as in step S26 (step S37). The binding of fluorescent label is thereby stopped.

The liquid in the columns 201 of the first specimen preparation section (Ac1), the third specimen preparation section (Ac3), the fourth specimen preparation section (Ac4), the fifth specimen preparation section (Ac5), the seventh specimen preparation section (Ac7), and the eighth specimen preparation section (Ac8) are injected to six wells of the solid phase tip for protein 101, and the solid phase tip for protein 101 is then aspirated from the lower side (step S38). The Histon H1 containing phosphate group bound with fluorescent labeled substance is thereby solid-phased on the porous film of the phase tip for protein 101.

The well is washed as in step S21 in the process of preparing expression level measurement reagent (step S39).

Finally, an operation of dispensing and discharging quenching reagent for quenching (background quenching) the fluorescent light based on the fluorescent labeled substance that has not bind to the phosphate group introduced into the Histon H1 into wells is repeated for six times (step S40). The body controller 10 then returns the process to step S5 of main routine shown in FIG. 15.

(6) Analyzing Process

Figure 19:
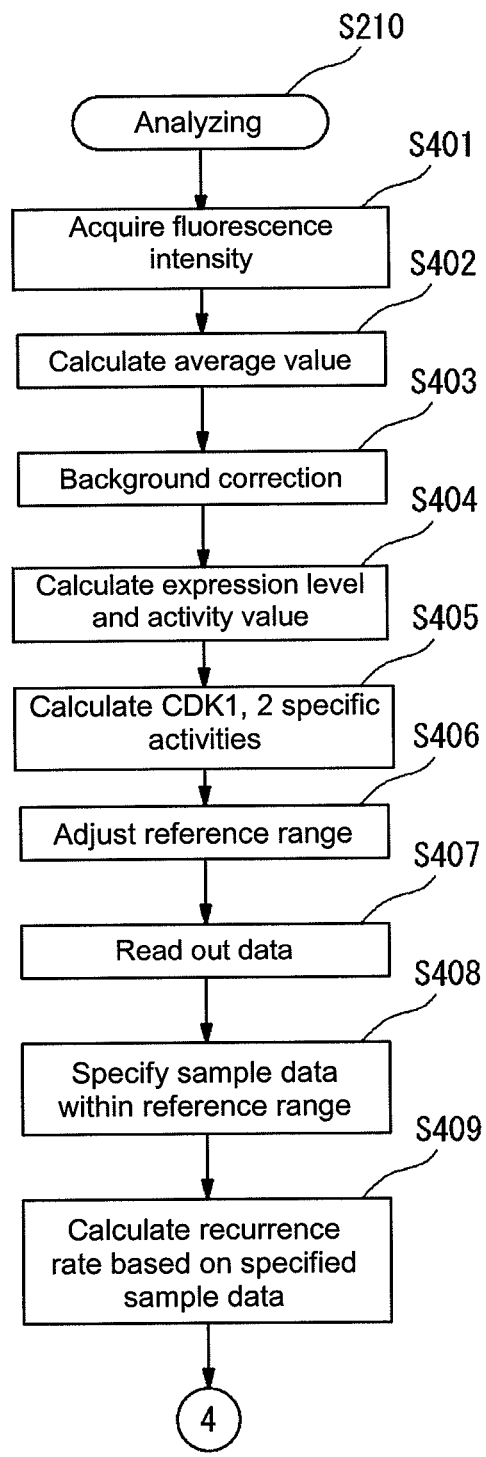
FIG. 19 is a view showing an overall flow of one example of an analyzing process in the diagnosis support device.
Figure 20:
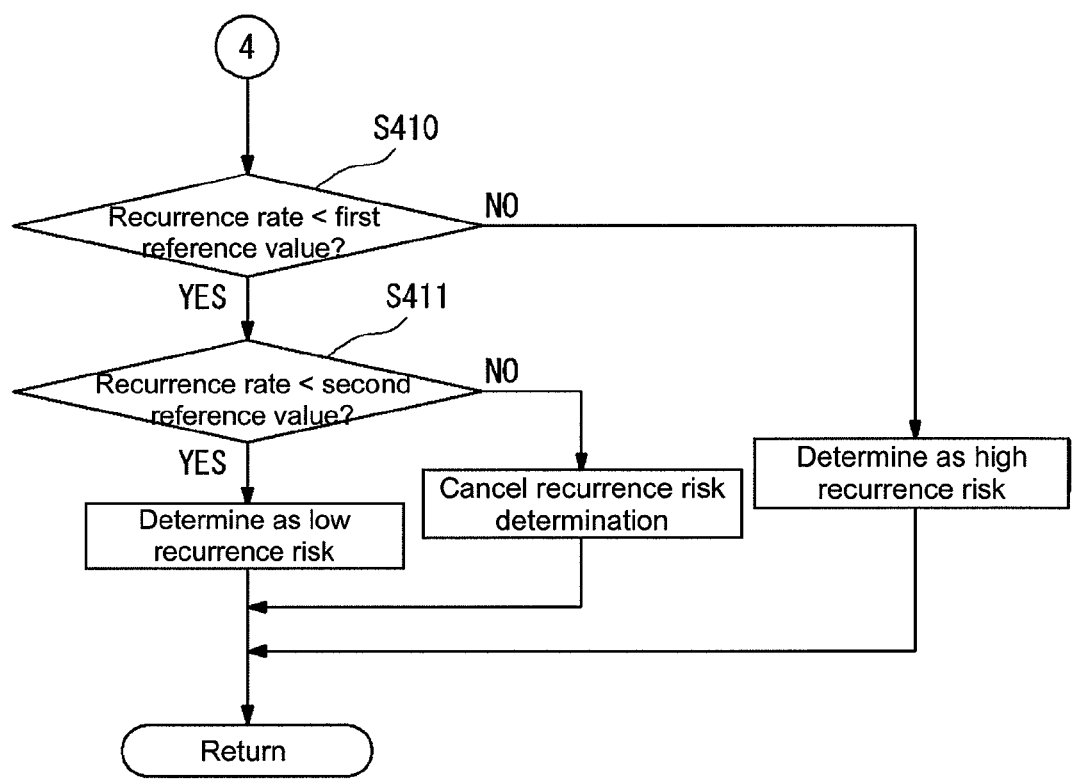
FIG. 20 is a view showing an overall flow of one example of an analyzing process by the diagnosis support system.

As shown in FIGS. 19 and 20, in the step of analyzing process (step S210), analysis is performed from the fluorescence intensity obtained in the detecting section, and the result of analysis is output to the display section 79.

First, in step S401, the controller 77 acquires two fluorescent intensities for each of activity of CDK1, expression of CDK1, activity of CDK2, expression of CDK2, activity of background, and expression of background through the body controller 10 from the light receiving system of the detecting section 4.

Thereafter, the controller 77 calculates the average value of the fluorescence intensities obtained two at a time for each item.

In step S403, the background activity (average value) is subtracted from the fluorescence intensity (average value) of the CDK1 activity. The background activity (average value) is subtracted from the fluorescence intensity (average value) of the CDK2 activity. The background correction is thus performed for the CDK1 activity and the CDK2 activity. The background correction is similarly performed for the CDK1 expression and the CDK2 expression.

In step S404, the controller 77 acquires the expression level and the activity value by using standard curve for each item. The standard curve is data for converting fluorescence intensity to expression amount or activity value. The standard curve is created in advance by using two or more types of samples which expression amount or activity value is known when the lot of the reagent is changed, and stored in the hard disc 91g of the controller 77.

In step S405, the controller 77 calculates the CDK1 specific activity and the CDK2 specific activity according to the following equation:

CDK1 specific activity=CDK1 activity value/CDK1 expression level

CDK2 specific activity=CDK2 activity value/CDK2 expression level

Step S405 may be a step in which the controller 77 calculates the inverse number of the CDK1 specific activity and the increase number of the CDK2 specific activity according to the following equation:

Inverse number of CDK1 specific activity=CDK1 expression level/CDK1 activity value Inverse number of CDK2 specific activity=CDK2 expression level/CDK2 activity value Thereafter, in step S406, the controller 77 determines the reference range. The reference range is a region including sample data having a measurement value approximate to a measurement value (CDK1 specific activity and CDK2 specific activity) of a predetermined measurement item (CDK1 specific activity and CDK2 specific activity) related to a malignant tumor of a cancer patient to be diagnosed. The reference range is determined as a circle having a preset radius with a measurement value as a center.

In step S407, the controller 77 reads out sample data in which the measurement value such as activity values and expression levels of other cancer patients and the clinical information on other patients from the second database 91j of the hard disc 91g.

In step S408, the controller 77 searches for and specifies the sample data having a measurement value (CDK1 specific activity and CDK2 specific activity) within the reference range determined in step S406.

In step S409, the controller 77 calculates a recurrence rate based on the sample data specified in step S408. Specifically, the recurrence rate is calculated by counting the total number of other cancer patients having the measurement value in the reference range based on the sample data of the other cancer patients specified in step S408, and calculating the percentage including the recurred cancer patient. The recurrence rate is shown in percentage (%) with the total number of other cancer patients having the measurement value in the reference range as 100.

Thereafter, in step S410 and step S411, the recurrence risk is determined by comparing the calculated recurrence rate and the reference value set in advance.

First, in step S410, the controller 77 determines whether or not the recurrence rate is smaller than a first reference value, and advances the process to step S411 if Yes, and determines that the recurrence risk is "high" if No. The first reference value herein is 14%.

In step S411, the controller 77 determines whether or not the recurrence rate is smaller than a second reference value, and determines that the recurrence risk is "low" if Yes, and determines to cancel the determination if No. The second reference value herein is 5%.

The reference value may be one, or three or more. The recurrence risk may be determined in two stages, "high" and "low", or may be segmentalized and determined in three or more stages of recurrence risk "high", "intermediate", and "low".

Thereafter, in step S211, the controller 77 displays, on the display screen of the display unit, the CDK1 specific activity and the CDK2 specific activity serving as a basis of determining the recurrence rate, the recurrence risk, and the like by plotting on the distribution diagram, as well as the reference range on the distribution diagram, and furthermore, personal information on the cancer patient to be diagnosed such as personal number and age, measurement value of a predetermined item of the malignant tumor, recurrence rate, determination result of the recurrence risk, and the like, as shown in FIG. 21 and FIG. 22 (step S211). The distribution diagram of the display screen shown in FIG. 21 displays the CDK1 specific activity in logarithm on the horizontal axis and displays the CDK2 specific activity in logarithm on the vertical axis. On the display screen shown in FIG. 22, the disease free survival, the recurrence rate, the determination result of the recurrence risk (in the figure, "risk determination") and the like in a case where hormone therapy is performed are displayed. The controller 77 returns the process to step S211 of the main routine shown in FIG. 15.

In the embodiment described above, the controller 77 acquires two fluorescent intensities for each of activity of CDK1, expression of CDK1, activity of CDK2, expression of CDK2, activity of background, and expression of background, and calculates the average value of the fluorescence intensities obtained two at a time for each item in step S401, but is not limited thereto, and may acquire three or more fluorescent intensities for each of activity of CDK1, expression of CDK1, activity of CDK2, expression of CDK2, activity of background, and expression of background, and calculate the average value of the fluorescence intensities obtained for each item. One fluorescent intensity may be acquired for each of activity of CDK1, expression of CDK1, activity of CDK2, expression of CDK2, activity of background, and expression of background. In this case, the background corrections of the activity and the expression of the CDK1 as well as the activity and the expression of the CDK2 are performed using the fluorescent intensity of each item acquired one at a time instead of the average value of the respective item in step S403.

In the present embodiment, the user such as doctor appropriately sets the radius of the reference range, and the reference range is determined as the circle of the set radius. The reference range is desirably determined to a size capable of ensuring the required minimum number of samples to ensure statistical reliability. Therefore, from the standpoint of ensuring reliability, the information on the number of samples contained in the reference range may be displayed at the same time as the display of the reference range on the display screen so as to ensure the required minimum number of samples in the reference range. The user references the information on such number of samples displayed on the screen, and can easily reset the radius of the reference range to that which ensures an appropriate number of samples.

The diagnosis support system may automatically determine the radius of the reference range. When the diagnosis support system automatically sets the radius, for example, the radius is preferably set such that:

(I) a region having a predetermined size including data on a certain number of cancer patients, having medical and statistical meaning with the measurement value of the predetermined measurement item related to the malignant tumor of the cancer patient to be diagnosed as a center point is set;

(II) a region having a predetermined size including a measurement value of a predetermined measurement item related to the malignant tumor of the cancer patient to be diagnosed and the measurement error/standard deviation by the system is set; and (III) a region having a predetermined size including a measurement value of a predetermined measurement item related to the malignant tumor of the cancer patient to be diagnosed and the measurement error/standard deviation of the measurement value obtained by measuring for one or more times the one predetermined measurement item for one specimen is set.

The controller 77 can provide diagnosis support information with higher precision having medical meaning by determining the reference range as (I). The controller 77 can determine the reference range as (II) to prevent lowering in accuracy due to the measurement error by the system. Furthermore, the controller 77 can determine the reference range as (III) to prevent lowering in accuracy due to variation in the measurement value by the measurement method. The diagnosis support information with high precision can be provided as the reference range is determined in the above manner in step S406.

In the present embodiment, the reference range is a circle having a measurement value as a center, but may be other shapes such as square or ellipse having the measurement value as a center.

EXAMPLES

The result obtained by analyzing the malignant tumors collected from five cancer patients (cancer patients 1 to 5) to be diagnosed by using the above-described diagnosis system is shown below.

Reference Example

The activity values and the expression levels of the CDK1 and the CDK2 in a malignant tumor of a patient with breast cancer were measured. The specific activity of the CDK1, the specific activity of the CDK2, and the ratio of the specific activity of the CDK1 and the specific activity of the CDK2 were calculated from the obtained activity values and the expression levels. The distribution diagram was then created with the vertical axis as the log value of the specific activity of the CDK2 and the horizontal axis as the log value of the specific activity of the CDK1.

The following reference values were set as the reference value used for risk determination.
1) Ratio of the specific activity of CDK1 and the specific activity of CDK2 (specific activity ratio) is 5.0
2) low reference value: specific activity of CDK1 is 6
3) intermediate reference value: specific activity of CDK1 is 20
4) high reference value: specific activity of CDK1 is 90

The eight regions segmented by four reference values are set to any one of "high" recurrence risk (H), "intermediate" recurrence risk (I), or "low" recurrence risk (L). Specifically, the region greater than the reference value related to the specific activity ratio and greater than the intermediate reference value is "high" (H) region. The region greater than the reference value related to the specific activity ratio, smaller than the intermediate reference value, and greater than the low reference value is "intermediate" (I) region. Furthermore, the region greater than the reference value related to the specific activity ratio and smaller than the low reference value is "low" (L) region. With respect to the region smaller than the reference value related to the specific activity ratio, the region greater than the high reference value is "high" (H) region, and the region smaller than the high reference value is "low" (L) region.

Example 1

The activity values and the expression levels of the CDK1 and the CDK2 of the malignant tumor of cancer patient 1 were measured, and the logarithmic (log) values of the respective specific activities of the CDK1 and the CDK2 were calculated. As a result, the logarithmic (log) value of the specific activity of the CDK1 was 1.7, and the logarithmic (log) value of the specific activity of the CDK2 was 1.8. With a large-scale clinical test result of a sample of a no therapy group+hormone therapy group+chemotherapy by anthracyclin group as a reference data set, the recurrence risk of cancer patient 1 was determined according to the reference example and was found to belong to "low (L)" region.

With a large-scale clinical test result of a sample of a no therapy group+hormone therapy group+chemotherapy by anthracyclin group as a reference data set based on the calculated logarithmic (log) value of the specific activity, the distribution diagram was created as in a reference example by the diagnosis support system of the present invention, and the recurrence rate was calculated.

Figure 24:
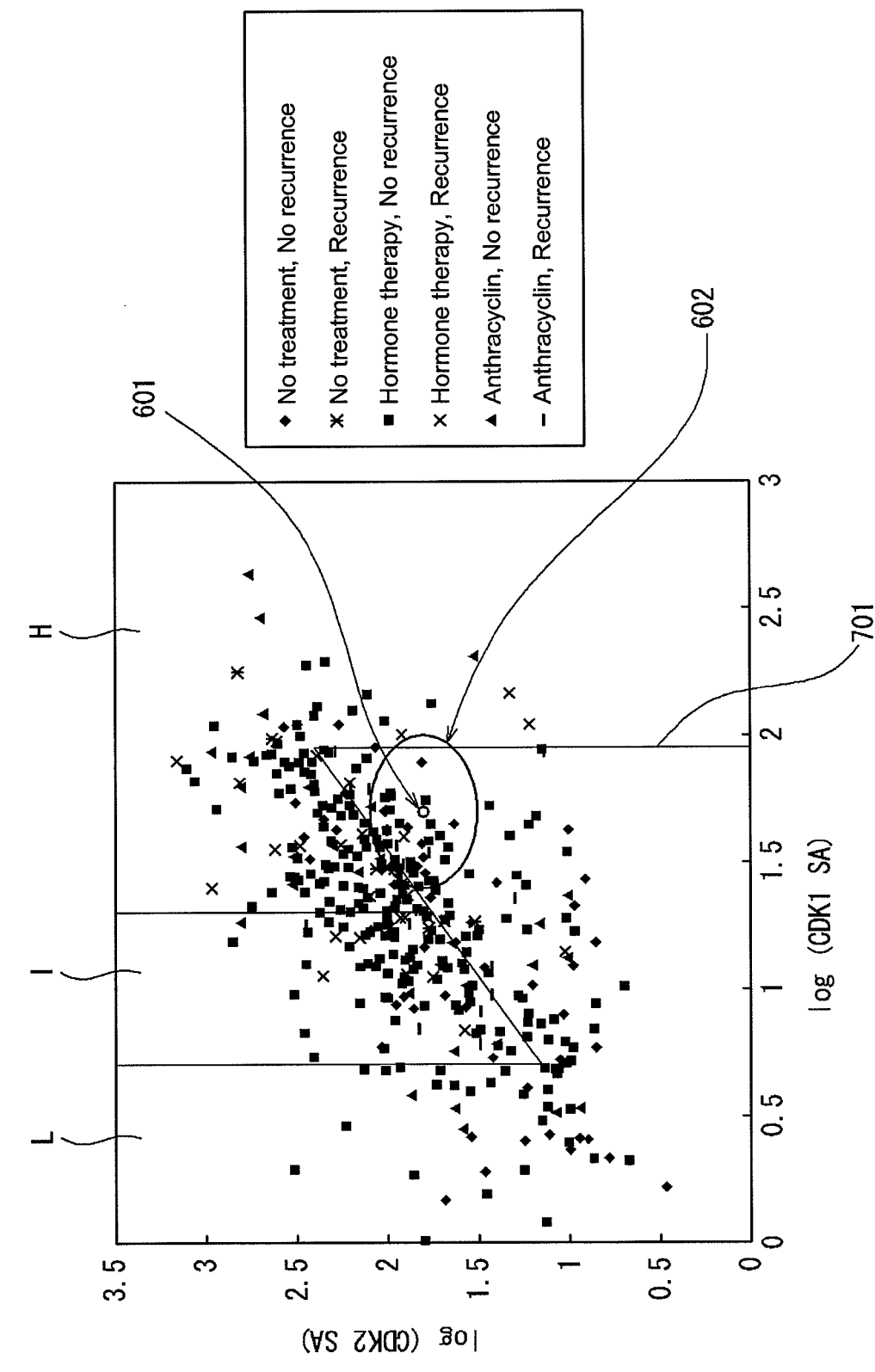
FIG. 24 is a view showing an example of diagnosis support information by the diagnosis support system.
Figure 25:
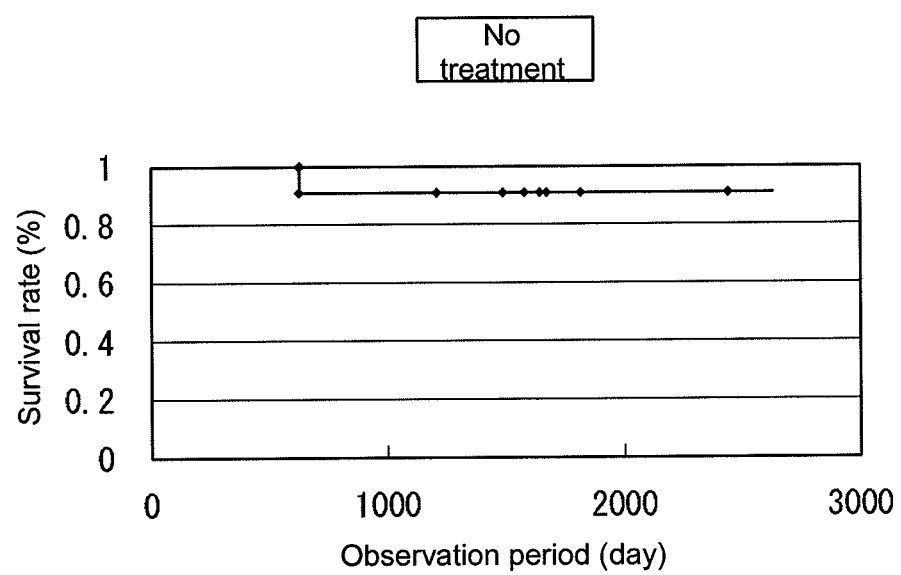
FIG. 25 is a view showing an example of diagnosis support information by the diagnosis support system.
Figure 26:
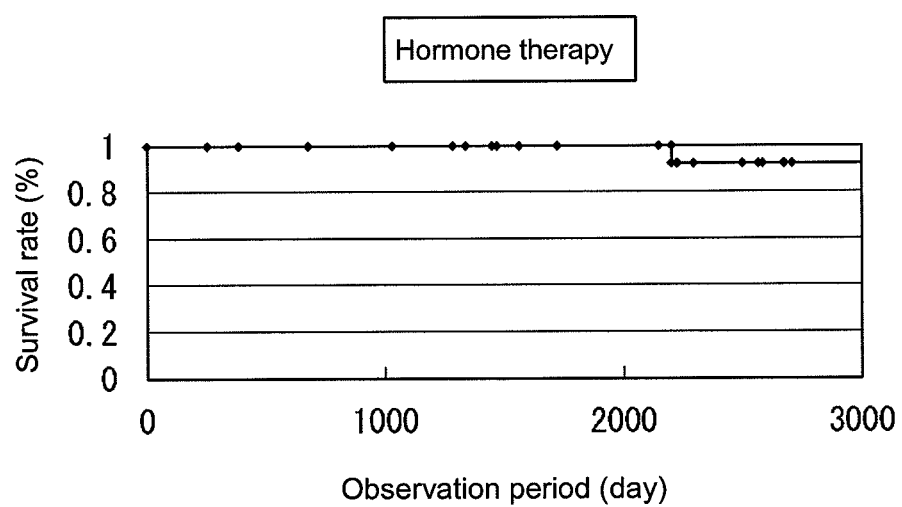
FIG. 26 is a view showing an example of diagnosis support information by the diagnosis support system.
Figure 27:
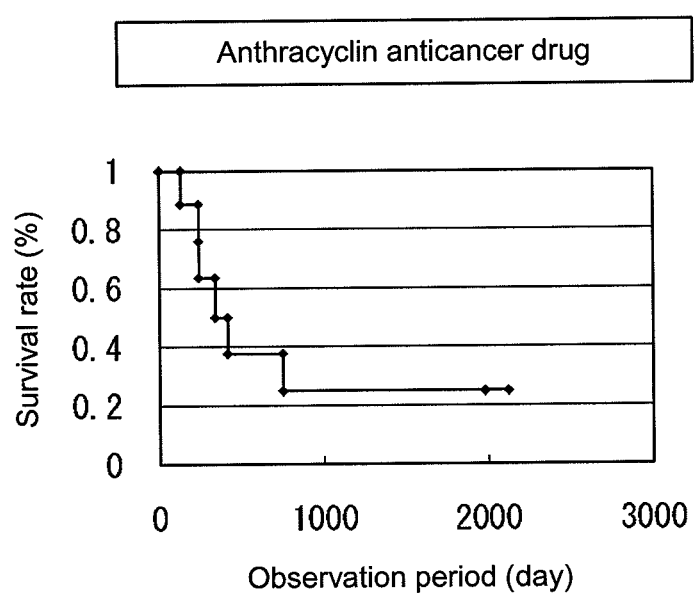
FIG. 27 is a view showing an example of diagnosis support information by the diagnosis support system.

The size (radius) of the reference range on the measurement value of the cancer patient 1 was 0.3. FIG. 24 to FIG. 27 show examples of the diagnosis support information by the diagnosis support system of the present invention. In FIG. 24, the distribution diagram of the measurement values of the CDK1 and the CDK2 of the malignant tumor are shown. In FIG. 24, "high" (H) region, "intermediate" (I) region, and "low" (L) region are displayed together based on a threshold value 701 by the reference example. In FIG. 25 to FIG. 27, the result of the survival curve predicted when each therapy is performed is shown. In the graph of each survival curve shown in FIG. 25 to FIG. 27, the vertical axis shows a disease free survival, and the horizontal axis shows an observation period (day). The determination reference of the recurrence risk is "high risk" when the recurrence rate is greater than or equal 14%, and "low risk" when the recurrence rate is smaller than 5%.

In the distribution diagram shown in FIG. 24, the measurement value 601 of cancer patient 1 is displayed, and a reference range 602 is also displayed. As shown in FIG. 24, the measurement value 601 of cancer patient 1 belongs to "low" (L) region according to the recurrence risk determination of the reference example, but information on other cancer patients belonging to the vicinity of the threshold value having an approximate measurement value or the "high" (H) region is provided as the diagnosis support information according to the diagnosis support system of the present embodiment. A more appropriate determination thus becomes possible. If no therapy is carried out on the cancer patient 1 from the information on the cancer patient 1 provided by the diagnosis support system of the present embodiment and other cancer patients having approximate measurement values, the recurrence rate is predicted to be 9.1%. Similarly, if hormone therapy is carried out on the cancer patient 1, the recurrence rate is predicted to be 3.8%. Furthermore, if chemotherapy by anthracyclin is performed on the cancer patient 1, the recurrence rate is predicted to be 75%, and the possibility that the chemotherapy by anthracyclin is not effective is predicted with respect to the malignant tumor of cancer patient 1.

As shown in FIG. 25 and FIG. 26, respectively, if no therapy is carried out on the cancer patient 1, lowering in disease free survival in about 800 days is predicted, but if hormone therapy is carried out, the disease free survival is predicted to be maintained to at least about 2200 days. Thus, according to the diagnosis support system of the present embodiment, information serving as an index for determining that hormone therapy is one of the effective means can be provided to the cancer patient 1. As shown in FIG. 25 and FIG. 27, respectively, if no therapy is carried out on the cancer patient 1, lowering in disease free survival in about 800 days is predicted, and if chemotherapy by anthracyclin is carried out, lowering in disease free survival in about 100 days is predicted. Thus, according to the diagnosis support system of the present embodiment, information serving as an index for determining that anthracyclin therapy may not be effective can be provided to the cancer patient 1.

From such results, according to the diagnosis support system of the present embodiment, diagnosis support information corresponding to each patient can be provided, the recurrence rate by therapy to be adopted in the future can be predicted at high precision, thereby suggesting provision of information for selecting a more suitable therapy to each patient.

The survival curve may be a survival curve created from information on survival/death of the clinical information on other cancer patients.

Example 2

The activity values and the expression levels of the CDK1 and the CDK2 of the malignant tumor of cancer patient 2 were measured, and the logarithmic (log) values of the respective specific activities of the CDK1 and the CDK2 were calculated. As a result, the logarithmic (log) value of the specific activity of the CDK1 was 1.5, and the logarithmic (log) value of the specific activity of the CDK2 was 2.5. With a large-scale clinical test result (332 samples) of a sample of a no therapy group+hormone therapy group as a reference data set, the recurrence risk of cancer patient 2 was determined according to the reference example and was found to belong to "high (H)" region.

With a large-scale clinical test result (332 samples) of a sample of a no therapy group+hormone therapy group as a reference data set based on the calculated logarithmic (log) value of the specific activity, the distribution diagram was created by the diagnosis support system of the present invention, and the recurrence rate was calculated. The size (radius) of the reference range on the measurement value of cancer patient 2 was 0.15.

Figure 28:
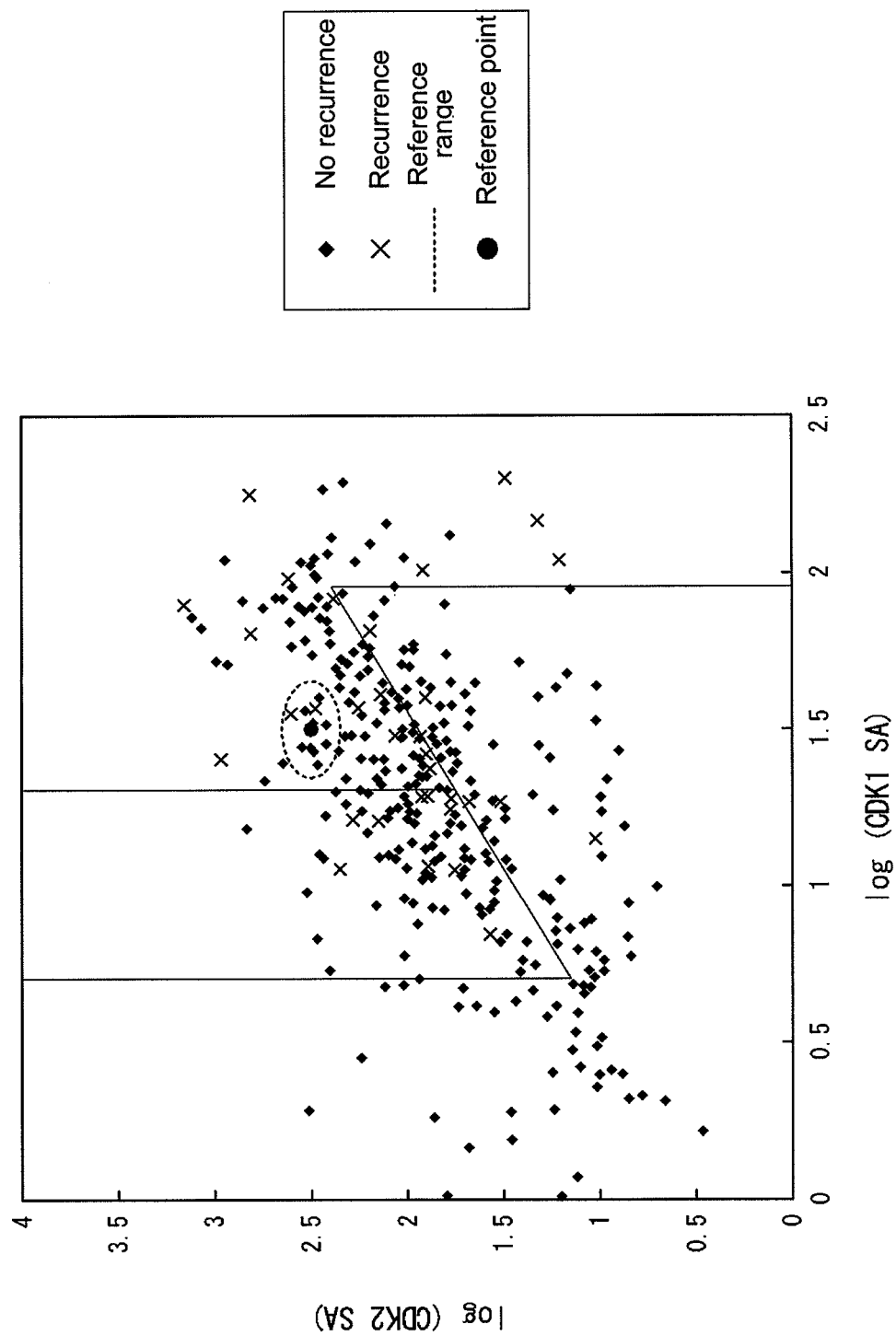
FIG. 28 is a view showing an example of diagnosis support information by the diagnosis support system.

FIG. 28 shows an example of the diagnosis support information by the diagnosis support system of the present embodiment. As shown in FIG. 28, according to the diagnosis support system of the present embodiment, information on other cancer patients having a measurement value approximate to the cancer patient 2 provided by the diagnosis support system of the present embodiment is shown within the reference range, and can be provided as information useful for more suitably diagnosing the cancer patient 2.

With respect to cancer patient 2, according to the information on other cancer patients having a measurement value approximate to the cancer patient 2 provided by the diagnosis support system of the present embodiment, the reference range includes two patients with recurrence and nine patients without recurrence. The recurrence rate was predicted based thereon, and was predicted to be 18.2%.

Example 3

Similar to the second example, the activity values and the expression levels of the CDK1 and the CDK2 of the malignant tumor of cancer patient 3 were measured. As a result, the logarithmic (log) value of the specific activity of the CDK1 was 1.5, and the logarithmic (log) value of the specific activity of the CDK2 was 2. The recurrence risk of the subject cancer patient was determined according to the reference example and was found to belong to "high (H)" region.

Figure 29:
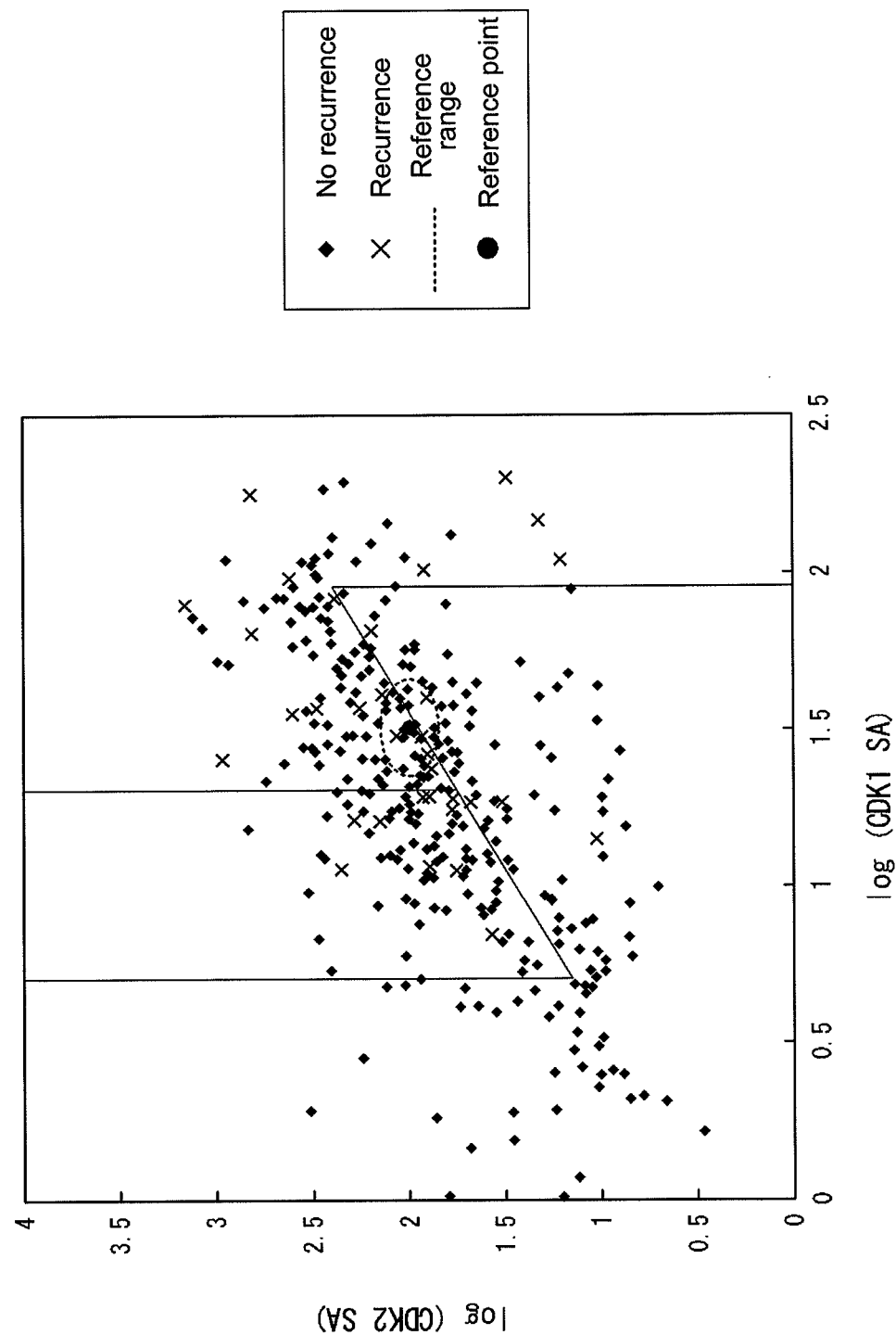
FIG. 29 is a view showing an example of diagnosis support information by the diagnosis support system.

FIG. 29 shows an example of the diagnosis support information by the diagnosis support system of the present embodiment. As shown in FIG. 29, according to the diagnosis support system of the present embodiment, information on other cancer patients having a measurement value approximate to the cancer patient 3 provided by the diagnosis support system of the present embodiment is shown within the reference range, and can be provided as information useful for more suitably diagnosing the cancer patient 3.

The recurrence rate was predicted from the information on other cancer patients having a measurement value approximate to the cancer patient 3 provided by the diagnosis support system of the present embodiment. The reference range includes four patients with recurrence and twenty-one patients without recurrence. The recurrence rate was predicted based thereon, and was predicted to be 16.0%. Thus, when determined according to the reference example, the cancer patient 3 is determined as belonging to the "high" (H) region, similar to the cancer patient 2 of the second example, but according to the diagnosis support system of the present embodiment, the predicted recurrence rate differs between the cancer patient 3 of the present example and the cancer patient 2 of the second example. More specifically, the measurement value of the cancer patient 2 of the second example (specific activity of CDK1 and specific activity of CDK2) exists at a position distant from a boundary with the "low" (L) region or the "intermediate" (I) region in the "high" (H) region by the reference example, and the measurement value of the cancer patient 3 of the present example exists near the boundary with the "low" (L) region in the "high" (H) region by the reference example. The recurrence rate obtained by the diagnosis support system according to the embodiment is 18.2% for the cancer patient 2 of the second example, and the recurrence rate obtained by the diagnosis support system according to the embodiment is 16% for the cancer patient 3 of the third example. Therefore, in the diagnosis support system according to the embodiment, the recurrence rate corresponding to the measurement value of the cancer patient can be obtained, that is, the recurrence rate accurately reflecting the state of the malignant tumor of the cancer patient can be predicted.

Example 4

Similar to the second example, the activity values and the expression levels of the CDK1 and the CDK2 of the malignant tumor of cancer patient 4 were measured. As a result, the logarithmic (log) value of the specific activity of the CDK1 was 0.5, and the logarithmic (log) value of the specific activity of the CDK2 was 1. The recurrence risk of cancer patient 4 was determined according to the reference example and was found to belong to "low (L)" region.

Figure 30:
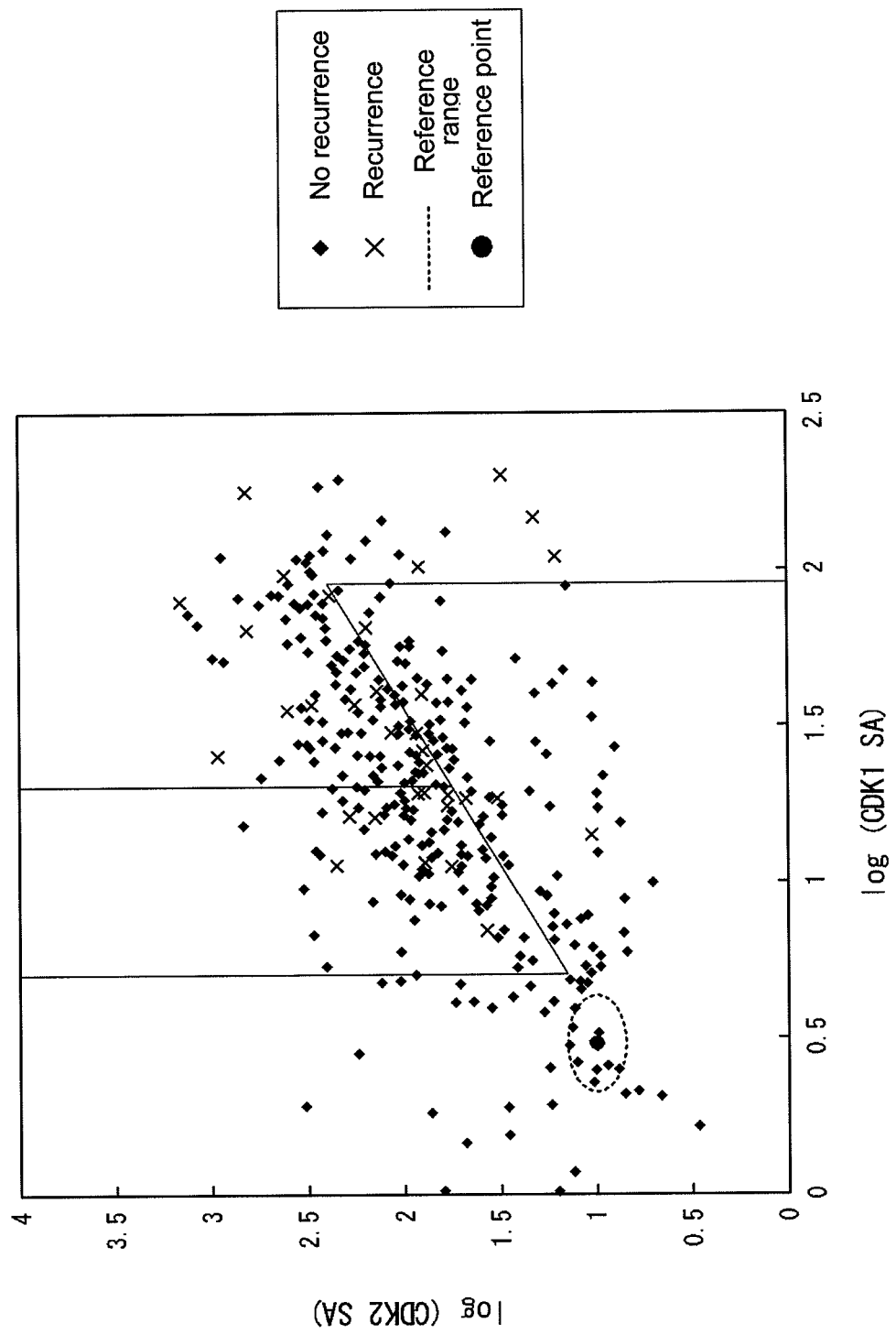
FIG. 30 is a view showing an example of diagnosis support information by the diagnosis support system.

FIG. 30 shows an example of the diagnosis support information by the diagnosis support system of the present embodiment. As shown in FIG. 30, information on other cancer patients having a measurement value approximate to the cancer patient 4 provided by the diagnosis support system of the present embodiment is shown within the reference range, and can be provided as information useful for more suitably diagnosing the cancer patient 4.

The recurrence rate was predicted from the information on other cancer patients having a measurement value approximate to the cancer patient 4 provided by the diagnosis support system of the present embodiment. The reference range includes zero patient with recurrence and eight patients without recurrence. Therefore, the recurrence rate was predicted to be 0%.

Example 5

Similar to the second example, the activity values and the expression levels of the CDK1 and the CDK2 of the malignant tumor of cancer patient 5 were measured. As a result, the logarithmic (log) value of the specific activity of the CDK1 was 1.2, and the logarithmic (log) value of the specific activity of the CDK2 was 1.5. The recurrence risk of cancer patient 5 was determined according to the reference example and was found to belong to "low (L)" region.

Figure 31:
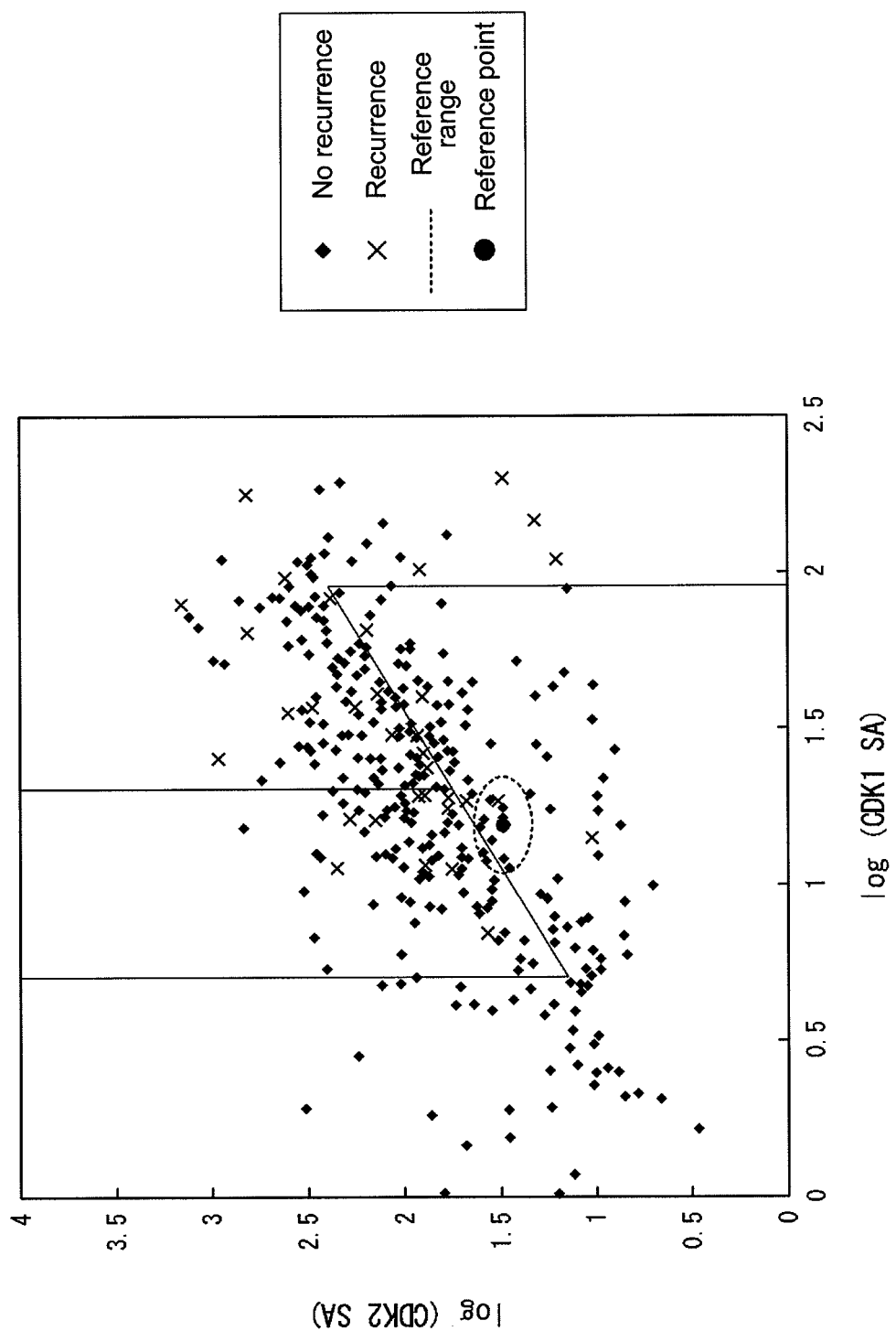
FIG. 31 is a view showing an example of diagnosis support information by the diagnosis support system.

FIG. 31 shows an example of the diagnosis support information by the diagnosis support system of the present embodiment. As shown in FIG. 31, information on other cancer patients having a measurement value approximate to the cancer patient 5 provided by the diagnosis support system of the present embodiment is shown within the reference range, and can be provided as information useful for more suitably diagnosing the subject cancer patient.

The recurrence rate was predicted from the information on other cancer patients having a measurement value approximate to the cancer patient 5 provided by the diagnosis support system of the present embodiment. The reference range includes one patient with recurrence and ten patients without recurrence. The recurrence rate was predicted based thereon, and was predicted to be 9.1%. Thus, when determined according to the reference example, the subject cancer patient of the fifth example is determined as belonging to the "low" (L) region, similar to the subject cancer patient of the fourth example, but according to the diagnosis support system of the present embodiment, the predicted recurrence rate differs between the cancer patient 5 of the present example and the cancer patient 5 of the fourth example. More specifically, the measurement value of the cancer patient 4 of the fourth example exists at a position distant from a boundary with the "high" (H) region or the "intermediate" (I) region in the "low" (L) region by the reference example, and the measurement value of the cancer patient 5 of the present example exists near the boundary with the "intermediate" (I) region in the "low" (L) region by the reference example. The recurrence rate obtained by the diagnosis support system according to the embodiment is 0% for the cancer patient 4 of the fourth example, and the recurrence rate obtained by the diagnosis support system according to the embodiment is 9.1% for the cancer patient 5 of the present example. Therefore, in the diagnosis support system according to the embodiment, the recurrence rate corresponding to the measurement value of the cancer patient can be obtained, that is, the recurrence rate accurately reflecting the state of the malignant tumor of the cancer patient can be predicted.

According to the diagnosis support system of the present embodiment, clinical information on other cancer patients having a measurement value approximate to the measurement value obtained by measuring a predetermined measurement item related to the malignant tumor of the cancer patient can be provided, and information enabling the doctors to diagnose cancer at high precision can be provided.

It should be apparent to those skilled in the art that the present invention may be embodied in many other specific forms without departing from the spirit or scope of the invention. Therefore, the present invention is not to be limited to the details given herein, but may be modified within the scope and equivalence of the appended claims.

What is claimed is:

1. A diagnosis support system for cancer, comprising:
a measurement value acquiring section for acquiring a measurement value of a first cancer patient, wherein the measurement value is generated by conducting measurement of two kinds of predetermined measurement items on a sample prepared by using a malignant tumor obtained from the first cancer patient;
a storage unit for storing sample data of a plurality of cancer patients different from the first patient, wherein the sample data comprise measurement values generated by conducting measurement of the two kinds of predetermined measurement items on each sample prepared by using a malignant tumor obtained from each of the plurality of cancer patients, clinical information after resection of malignant tumor of each of the plurality of the cancer patients, and a reference range;
a display unit; and
a controller programmed to retrieve the sample data for the plurality of measurement values and the reference range from the storage unit, and to display on the display a distribution chart in which the plurality of measurement values and the measurement value regarding the first cancer patient are plotted with the two kinds of the predetermined measurement items as coordinate axes and the reference range including the measurement value regarding the first cancer patient is represented, wherein
the controller controls the display unit to display a diagnosis support screen showing the clinical information included in the sample data having measurement value within the reference range.

2. The system according to claim 1, wherein the controller controls the display unit to display the distribution chart on the diagnosis support screen.

3. The system according to claim 1, further comprising:
a sample data specifying section for specifying the sample data having a measurement value within the reference range from the sample data stored in the sample data memory; and
an analyzing section for analyzing clinical information on the specified sample data, and generating result of analysis;
wherein the display controller controls the display unit so as to display the result of analysis.

4. The system according to claim 3, wherein the result of analysis comprises a recurrence rate of cancer, and/or, a recurrence risk of cancer, and/or, disease free survival.

5. The system according to claim 1, wherein the measurement value comprises values related to expression of a cell cycle protein and/or activity of the cell cycle protein.

6. The system according to claim 5, wherein the cell cycle protein is cyclin-dependent kinase (CDK).

7. The system according to claim 6, wherein the measurement value is a first ratio which is a ratio of an activity value and an expression level of a first CDK, and a second ratio which is a ratio of an activity value and an expression level of a second CDK.

8. The system according to claim 7, wherein the measurement value acquiring section further comprises,
an activity value/expression level acquiring section for acquiring the activity value and the expression level of the first CDK, and the activity value and the expression level of the second CDK, and
a calculating section for calculating the first ratio based on the activity value and the expression level of the first CDK, and the second ratio based on the activity value and the expression level of the second CDK.

9. The system according to claim 1, wherein the clinical information is information related to recurrence of cancer.

10. The system according to claim 9, wherein the clinical information further comprises information related to postoperative treatment and information related to presence/absence of survival.

11. The system according to claim 1, further comprising a measuring unit for obtaining a measurement value related to the first cancer patient by measuring the predetermined measurement item by using the sample prepared with a malignant tumor obtained from the first cancer patient.

12. A method of providing cancer diagnosis support information, comprising the steps of:
retrieving an input of a measurement value of a first cancer patient, wherein the measurement value is generated by conducting measurement of two kinds of predetermined measurement items on a sample prepared by using a malignant tumor obtained from the first cancer patient;
retrieving from a storage unit data for a plurality of measurement values and a reference range obtained by performing the measurement of the two kinds of predetermined measurement items on a specimen prepared by using malignant tumors obtained from a plurality of cancer patients other than the first cancer patient; and
displaying on a display a distribution chart in which the plurality of measurement values and the measurement value regarding the first cancer patient are plotted with the two kinds of predetermined measurement items as coordinate axes, and the reference range including the measurement value regarding the first cancer patient is represented,
retrieving from the storage unit clinical information; and
displaying on the display a diagnosis support screen showing clinical information included in the sample data having measurement value within the reference range.

13. The method according to claim 12 further comprising the steps of:
specifying the sample data having a measurement value within the reference range from the stored sample data; and
analyzing clinical information on the specified sample data, and generating result of analysis;
wherein the result of analysis is displayed in the display step.

14. The method according to claim 12, wherein the clinical information is information related to recurrence of cancer.

15. The method according to claim 14, wherein the clinical information further comprises information related to postoperative treatment and information related to presence/absence of survival.

16. A computer program product comprising:
a computer readable medium; and
instructions, on the computer readable medium, adapted to enable a computer to perform operations, comprising:
acquiring a measurement value of a first cancer patient, wherein the measurement value is a measurement value generated by conducting measurement of two kinds of predetermined measurement item on a sample prepared by using a malignant tumor obtained from the first cancer patient;
storing sample data of a plurality of cancer patients different from the first patient, wherein the sample data comprise measurement values generated by conducting measurement of the two kinds of predetermined measurement item on each sample prepared by using a malignant tumor obtained from each of the plurality of cancer patients, and clinical information after resection of malignant tumor of each of the plurality of the cancer patients;
determining a reference range based on the measurement value of the first cancer patient, wherein the measurement value of the first cancer patient is within the reference range; and
displaying a diagnosis support screen showing the clinical information included in the sample data having measurement value within the reference range.

17. A method according to claim 12, wherein the measurement value comprises values related to expression of a cell cycle protein and/or activity of the cell cycle protein.

18. A method according to claim 17, wherein the cell cycle protein is cyclin-dependent kinase (CDK).

19. A method according to claim 18, wherein the measurement value is a first ratio which is a ratio of an activity value and an expression level of a first CDK, and a second ratio which is a ratio of an activity value and an expression level of a second CDK.

20. A method according to claim 19, wherein the measurement value acquiring section further comprises,
an activity value/expression level acquiring section for acquiring the activity value and the expression level of the first CDK, and the activity value and the expression level of the second CDK, and
a calculating section for calculating the first ratio based on the activity value and the expression level of the first CDK, and the second ratio based on the activity value and the expression level of the second CDK.

21. The system according to claim 10, wherein the controller controls the display to display a diagnostic support screen showing a rate of cancer recurrence and/or a disease-free survival rate determined by the information on cancer recurrence and/or the information on survival after surgery of the cancer patients associated with the plurality of measurement values within the reference range.

22. The system according to claim 10, further comprising an input portion, and wherein upon receiving input for selecting a predetermined post-operative treatment at the input portion, the controller causes a rate of cancer recurrence and/or a disease-free survival rate of the cancer patients associated with the plurality of measurement values within the reference range and subjected to the selected post-operative treatment to be displayed on the diagnostic support screen.

23. The cancer diagnostic support system according to claim 21, wherein the storage unit stores a criterion value for determining risks of recurrence, and the controller causes determination results of risks of cancer recurrence obtained by the rate of cancer recurrence and the criterion value to be displayed on the diagnosis support screen.

24. The system according to claim 21, further comprising an input portion, wherein upon receiving an input for changing the range of the reference range displayed in the distribution chart at the input portion, the controller causes a rate of cancer recurrence and/or a disease-free survival rate of the cancer patients associated with the plurality of measurement values within the changed reference range to be displayed on the diagnostic support screen.

25. An apparatus for providing cancer diagnostic support information comprising:
an input receiver for receiving an input of a measurement value regarding a first cancer patient obtained by performing the measurement of two kinds of predetermined measurement items on a specimen prepared by using a malignant tumor obtained from the first cancer patient;

a storage unit for storing data including a plurality of measurement values obtained by performing the measurement of the two kinds of predetermined measurement items on specimens prepared by using malignant tumors obtained from a plurality of cancer patients other than the first cancer patient, clinical information after resection of malignant tumor of each of the plurality of cancer patients, and a reference range;

a display; and a controller programmed to retrieve the data for the plurality of measurement values and the reference range from the storage unit, and to display on the display a distribution chart in which the plurality of measurement values and the measurement value regarding the first cancer patient are plotted with the two kinds of measurement items as coordinate axes, and the reference range including the measurement value regarding the first cancer patient is represented, wherein the storage unit stores information on cancer recurrence and/or information on whether patients are alive or dead after surgery as the clinical information, and the controller controls the display to display a diagnostic support screen showing a rate of cancer recurrence and/or a disease-free survival rate determined by the information on cancer recurrence and/or the information on survival after surgery of the cancer patients associated with the plurality of measurement values within the reference range.

* * * * *